United States Patent [19]

Kenney et al.

[11] Patent Number: 5,484,778
[45] Date of Patent: * Jan. 16, 1996

[54] PHTHALOCYANINE PHOTOSENSITIZERS FOR PHOTODYNAMIC THERAPY AND METHODS FOR THEIR USE

[75] Inventors: Malcolm E. Kenney, Cleveland Heights; Nancy L. Oleinick, University Heights, both of Ohio; Boris D. Rihter, Wauwatosa, Wis.; Ying-Syi Li, Cleveland Heights, Ohio

[73] Assignee: University Hospitals of Cleveland, Cleveland, Ohio

[*] Notice: The portion of the term of this patent subsequent to Nov. 24, 2009, has been disclaimed.

[21] Appl. No.: 116,259

[22] Filed: Sep. 2, 1993

Related U.S. Application Data

[63] Continuation-in-part of Ser. No. 980,494, Nov. 23, 1992, abandoned, which is a continuation of Ser. No. 554,290, Jul. 17, 1990, Pat. No. 5,166,197.

[51] Int. Cl.$^6$ ............... C09B 47/04; C09B 47/08; A61K 31/555; A61K 31/685
[52] U.S. Cl. ............... 514/63; 514/43; 514/185; 514/191; 536/29.11; 540/123; 540/125; 540/128; 540/140
[58] Field of Search ............... 540/128, 140, 540/123, 125; 514/63, 185, 191, 43; 536/29.11

[56] References Cited

U.S. PATENT DOCUMENTS

| | | | |
|---|---|---|---|
| 4,927,735 | 5/1990 | Era et al. | 430/270 |
| 5,166,197 | 11/1992 | Kenney et al. | 514/63 |
| 5,358,940 | 10/1994 | Capraro et al. | 514/63 |

OTHER PUBLICATIONS

Ciliberto et al, Chem. Abstract 102:78944e (1985).
Doris et al, Chem. Abstract 108:178915p (1986).
"New Phthalocyanine Photosensitizers for Photodynamic Therapy," by Oleinick et al., *Photochemistry and Photobiology*, vol. 57, No. 2, p. 242–247, Feb. 1993.
"DNA Lesions and DNA Degradation in Mouse Lymphoma L5178Y Cells After Photodyamic Treatment Sensitized by Chloraluminum Phthalocyanine," by Ramakrishnan et al., *Photochemistry and Photobiology*, vol. 50, No. 3, pp. 373–378, Sep. 1989.
"Photodynamic Therapy Induces Rapid Cell Death by Apoptosis in L5178Y Mouse Lymphoma Cells," by Agarwal et al., *Cancer Research*, vol. 51, No. 51, pp. 5993–5996, Nov. 1, 1991.
"The Phthalocyanines: A New Class of Mammalian Cell Photosensitizers With a Potential for Cancer Phototherapy," by Ben–Hur et al., *Int. J. Radiat. Biol.*, vol. 47, No. 2, pp. 145–147, Feb. 1985.
"Activity of Phthalocyanine Photosensitizers Against Human Glioblastoma in Vitro," by Abernathy et al., *Neurosurgery*, 21, No. 4, pp. 468–473, Oct. 1987.
"The Role of Singlet Oxygen in the Photohemolysis of Red Blood Cells Sensitized by Phthalocyanine Sulfonates," by Sonoda et al., *Photochem. Photobiol.*, vol. 46, No. 5, pp. 625–631, Nov. 1987.
"Evaluation of Sulfonated Aluminum Phthalocyanines for Use in Photochemotherapy," by Bommer et al., *Cancer Letters*, vol. 44, pp. 7–15, 1989.
"The Effect of Substitutents on Phthalocyanine Phototoxicity," by Rosenthal et al., *Photochem. Photobiol.*, vol. 46, No. 6, pp. 959–963, Dec. 1987.
"Synthesis and Photocytotoxicity of Some New Substituted Phthalocyanines," by Leznoff et al., *Photochem. Photobiol.*, vol. 49, pp. 279–284, Mar. 1989.
*The Merck Manual*, 15th Edition, Robert Berkow, ed., pp. 1219–1220, 1227.
"The Nuclear Magnetic Resonance Spectra and the Electronic Spectra of Some Silicon and Germanium Phthalocyanines," Kane et al., *Inorganic Chemistry*, vol. 9, pp,. 1445–1448. (1970).
"Photodynamic Therapy With Phthalocyanine Photosensitisation: Quantitative Studies in a Transplantable Rat Eibrosarcoma" by Tralau et al., *Br. J Cancer*, vol. 55, No. 4, pp. 389–395, Apr. 1987.
"Biological Activities of Phthalocyanines—IX. Photosensitization of V–79 Chinese Hamster Cells and EMT–6 Mouse Mammary Tumor by Selectively Sulfonated Zine Phthalocyanines," by Brasseur et al., *Photochem. Photobiol.*, vol. 47, No. 5, pp. 705–711, May 1988.
"Tissue Uptake, Distribution and Potency of the Photoactivable Dye Chloraluminum Sulfonated Phthalocyanine in Mice Bearing Transplantable Tumors," by Chan et al., *Cancer Res.*, vol. 48, No. 11, pp. 3040–3044, Jun. 1, 1988.
"Photodynamic Therapy for Experimental Intraocular Melanoma Using Chloroaluminum Sulfonated Phthalocyanine," *Arch. Opthalmol.*, vol. 107, pp. 886–890, Jun. 1989, Panagopoulos.
"Synthesis of Positively Charged Phthalocyanines and Their Activity in the Photodynamic Therapy of Cancer Cells," by Wohre et al., *Photochem. Photobiol*, vol. 51, No. 3, pp. 351–356, Mar. 1990.
"Laser–Induced Photodynamic Therapy With Aluminum Phthalocyanine Tetrasulfonate as the Photosensitizer: Differential Phototoxicity in Normal and Malignant Human Cells in Vitro," by Glassberg et al., *J. Inv. Dermatol.*, vol. 94, No. 5, pp. 604–610, May 1990.

(List continued on next page.)

*Primary Examiner*—Philip I. Datlow
*Attorney, Agent, or Firm*—Calfee Halter & Griswold

[57] ABSTRACT

The present invention relates to a series of novel phthalocyanine compositions (or compounds) suitable for use as photosensitizers for photodynamic therapy. Specifically, the invention relates to a series of new aluminum (Al) germanium (Ge), gallium (Ga), tin (Sn) and/or silicon (Si) phthalocyanines having substituted amine or quaternary ammonium axial ligands attached to the central metal, and the use of these new phthalocyanine compositions for the treatment of cancer through photosensitization. Moreover, the present invention is directed to the methods of preparing these compositions for use in photodynamic therapy.

35 Claims, 4 Drawing Sheets

OTHER PUBLICATIONS

"Photodynamic Therapy of Spontaneous Cancers in Felines, Canines, and Snakes with Chloro–Aluminum Sulfonated Phthalocyanine," by Roberts et al., *J. Natl. Cancer Inst.*, vol. 83, No. 1, pp. 18–23, Jan. 2, 1991.

"Inactivation of Viruses in Red Cell and Platelet Concentrates With Aluminum Phthalocyanine (ALPc) Sulfonates," by Horowitz et al., *Blood Cells*, vol. 18, No. 1, pp. 141–150, Jan. 1992.

"Photodynamic Therapy of Chemically–and Ultraviolet B Radiation–Induced Murine Skin Papillomas by Chloroaluminum Phthalocyanine Tetrasulfonate," by Agarwal et al., *Photochem. Photobiol.*, vol. 56, No. 1, pp. 43–50, Jul. 1992.

"Biological Activities of Phthalocyanines—XVI. Tetrahydroxy–and Tetraalkylhydroxy Zinc Phthalocyanines. Effect of Alkyl Chain Length on In Vitro and In Vivo Photodynamic Activities," by Boyle et al., *Br. J. Cancer*, vol. 67, No. 6, pp. 1177–1181, Jun. 1993.

"Phthalocyanines in Photobiology," by I. Rosenthal and E. Ben–Hur, in *Phthalocyanines: Properties and Applications*, ed. by C. C. Leznoff and A. B. P. Lever, VCH Publishers, Inc., New York, pp. 397–425, 1989.

"Preclinical Examination of First and Second Generation Photosensitizers Used in Photodynamic Therapy," by C. J. Gomer, *Photochem. Photobiol.*, vol. 54, No. 6, pp. 1093–1107, Dec. 1991.

"Photodynamic Therapy in Oncology: Mechanisms and Clinical Use," H. I. Pass, *J. Natl. Can. Inst.*, vol. 85, No. 6, pp. 443–456, Mar. 17, 1993.

"Phthalocyanines as Photodynamic Sensitizers," by I, Rosenthal, *Photochem. Photobiol.*, vol. 53, No. 6, pp. 859–870, Jun. 1991.

PHTHALOCYANINE PHOTOSENSITIZERS FOR PHOTODYNAMIC THERAPY AND METHODS FOR THEIR USE

CROSS REFERENCE TO RELATED APPLICATIONS

This is a continuation-in-part of U.S. patent application Ser. No. 07/980,494, filed Nov. 23, 1992, now abandoned, which is a continuation application of U.S. patent application Ser. No. 554,290, filed Jul. 17, 1990, which issued as U.S. Pat. No. 5,166,197, Nov. 24, 1992.

BACKGROUND OF THE INVENTION

The present invention is directed to a series of novel phthalocyanines suitable for use as photosensitizers for photodynamic therapy. More particularly, the present invention is directed to a series of new aluminum (Al) and silicon (Si) phthalocyanines having substituted amine or quaternary ammonium axial ligands, and the use of these new phthalocyanine compositions for the therapeutic treatment of cancer. In addition, the present invention is directed to the methods of synthesizing these new compositions.

Photodynamic therapy, hereinafter also referred to as "PDT", is a relatively new process for treating cancer wherein visible light is used to activate a substance, such as a dye or drug, which then attacks, through one or more photochemical reactions, the tumor tissue thereby producing a cell killing, or cytotoxic, effect. It has been discovered that when certain non-toxic photodynamic sensitizers, such as hematoporphyrin derivative ("HpD" or "Photofrin® I"), which is extracted from serum and/or components thereof, are applied intravenously, topically, intradermally, etc., to the human or animal body, they are selectively retained by the cancerous tissue while being eliminated by the healthy tissue. As a result, after the administration of a photodynamic substance and the waiting of a certain period of time depending upon the type of photosensitizer utilized (i.e. two to three days after HpD treatment), substantially higher levels of the photosensitizer are retained in the cancerous tissue.

The tumor or cancerous tissue containing the photosensitizer can then be exposed to therapeutic light of an appropriate wavelength and at a specific intensity for activation. The light can be directly applied through the skin to the cancerous area from a conventional light source (e.g. laser, sun lamp, white light sources with appropriate filters, etc.), or in cases where the cancerous tissue is located deeper within the body, through surgical or non-surgical entry such as by the use of fiber optic illumination systems, including flexible fiber optic catheters, endoscopic devices, etc. The light energy and the photosensitizer cause a photochemical reaction which kills the cell in which the photosensitizer resides.

As a result, by applying a photosensitizer to the animal or human body, waiting for a sufficient period of time for the photosensitizer to permeate throughout the body while dissipating from normal tissue more rapidly than from cancer tissue, and exposing the cancerous region during the sensitive period to suitable light of sufficient intensity, the preferential destruction of the cancerous tissue will occur.

The mechanisms by which the photosensitizers produce their killing effect on the host cells upon illumination by an appropriate light source are not precisely defined and are the subject of continuing research. However, it is thought that there are at least two general mechanisms by which the photosensitizers are chemically altered upon illumination. The first general reaction mechanism involves energy transfer from the excited photosensitizer to oxygen present in the cancerous tissue. The excited photosensitizer transfers its additional energy to the oxygen, producing singlet molecular oxygen (SMO or $^1O_2$) which consequentially alters essential cell components.

More particularly, in the first general reaction mechanism, it is thought that the light energy causes the photosensitizer to become excited from the ground state, $S_0$, to the first excited singlet state, $S_1$. The photosensitizer's excited singlet state, $S_1$, is then transformed by intramolecular coupling to the lowest lying triplet state $T_1$. Through a direct intermolecular process discussed more particularly by John G. Parker of The John Hopkins University, Baltimore, Md., in U.S. Pat. Nos. 4,576,173; 4,592,361; and 4,827,938, the photosensitizer transfers this energy to oxygen molecules present in the tissue and raises them from the ground triplet to the first excited electronic singlet state $^1O_2$. The singlet molecular oxygen, $^1O_2$, destroys or alters vital cellular components such as the cell membrane, etc., ultimately inducing necrosis and destroying the cancerous tissue.

The process by which biological damage occurs as a result of the optical excitation of a photosensitizer in the presence of oxygen is generally referred to as "photodynamic action". A more detailed discussion concerning the use of photodynamic action in the treatment of cancer is discussed by Thomas J. Dougherty, William R. Potter, and Kenneth R. Weishaupt of Health Research, Inc., Buffalo, N.Y., in a series of patents, i.e. U.S. Pat. Nos. 4,649,151; 4,866,168; 4,889,129; and 4,932,934, concerning improved hematoporphyrin and porphyrin derivatives including dihematoporphyrin ether (DHE), the purified form of HpD, and methods utilizing same, for photodynamic therapy.

The second general mechanism thought to be involved in the killing effect produced by certain photosensitizers involves the production of free radicals. Subsequent reactions of the radicals with organic molecules and/or with oxygen results in the biochemical destruction of the diseased tissue.

Although the exact effective mechanisms of the photochemical reactions which produce death of the cancer cells is not clearly understood and varies depending upon the type of photosensitizer utilized, what is clear is that photodynamic therapy is effective for the preferential destruction of cancerous tissue. Furthermore, photodynamic therapy has several attractive features over conventional methods for treating cancer such as chemotherapy, radiation, surgical procedures, etc., in that the photosensitizers utilized are generally non-toxic, concentrate or remain preferentially in cancer cells, can be utilized with other modes of treatment since PDT does not interfere with other chemicals or processes, etc.

As a result, photodynamic therapy is now used experimentally for the treatment of malignant diseases in humans and animals. For example, photodynamic therapy has been used successfully for the treatment of a broad range of cancers including metastatic breast tumors, endometrial carcinomas, bladder tumors, malignant melanoma, Kaposi's sarcoma, basal cell carcinoma, chondrosarcoma, squamous cell carcinoma, prostate carcinoma, laryngeal papillomas, mycosis fungoides, superficial cancer of the tracheobronchial tree, cutaneous/mucosal papilloma, gastric cancer, enteric cancer, etc.

The drug in current clinical use is "Photofrin® II" a purified version of hematoporphyrin derivative (HpD, or "Photofrin® I"). HpD and Photofrin® II are complex mixtures of substances and have been the subject of numerous investigations to identify their active compounds. In addition, other porphyrins and porphyrin-like compounds such as chlorins (see U.S. Pat. Nos. 4,656,186; 4,693,885; and 4,861,876) and enlarged porphyrins, naphthalocyanines, phthalocyanines, platyrins, porphycenes (see U.S. Pat. Nos. 4,649,151 and 4,913,907), purpurins, texaphyrins, and verdins have been investigated as photosensitizers. Numerous other substances, such as "merocyanine 540", xanthenes (Rhodamine 123 6 G&B) cationic cyanic dyes, chalcogenapyryllium dyes, phenothiazinium derivatives, tetracycline, berbine sulphate, acridine orange, and fluorescein have also been used as photosensitizers, however, the porphyrin derivatives are generally preferred because they absorb in the long wave length region (red region) of the visible spectrum.

The specific reactions used by many of the above substances to produce the killing effect in cancer cells on exposure to excitatory light are in most instances not known or well understood. As mentioned above, research continues in this area in order to more fully understand the cytotoxic effects produced by the various photosensitizers.

Notwithstanding the above, although many of the above identified substances have demonstrated enhanced effects in photodynamic therapy, these substances also produce various side effects which limit their use for photodynamic therapy. The most predominant side effect exhibited by many of the currently utilized substances is the development of uncontrolled photosensitivity reactions in patients after the systemic administration of the photosensitizer and the exposure of the patient to normal sunlight. In this regard, on exposure to the sun, the photodynamic therapy patients can develop generalized skin photosensitization. As a result, the patient after receiving systemic injections of a photosensitizing substance is required to avoid bright light, especially sunlight for periods of about four to eight weeks.

Furthermore, since many of the above photosensitizers bind to other non-cancerous cells, some healthy cell destruction can also occur. Similarly, although many of the photosensitizers are soluble in water, large dosages are required for cellular uptake and/or treatment. Thus, use of many of the above indicated photosensitizers is normally limited to patients with severe cancerous tumors and continuing research is being conducted in order to produce photosensitizing substances, and/or methods of administering such substances, that avoid these side reactions as well as produce enhanced photosensitizing effects.

Considerable attention has recently been directed to a group of compounds having the phthalocyanine ring system. These compounds, called phthalocyanines, hereinafter also abbreviated as "Pc", are a group of photoactive dyes that are somewhat structurally similar (i.e. have nitrogen containing ring structure) to the porphyrin family. Phthalocyanines are azaporphyrins consisting of four benzoindole nuclei connected by nitrogen bridges in a 16-membered ring of alternating carbon and nitrogen atoms around a central metal atom (i.e. $C_{32}H_{16}N_8M$) which form stable chelates with metal cations. In these compounds, the ring center is occupied by a metal ion (such as a diamagnetic or a paramagnetic ion) that may, depending on the ion, carry one or two simple ligands. In addition, the ring periphery may be either unsubstituted or substituted.

Since E. Ben-Hur and I. Rosenthal disclosed the potential use of phthalocyanines as photosensitizers in 1985 (E. Ben-Hur and I. Rosenthal, The phthalocyanines: A new class of mammalian cell photosensitizers with a potential for cancer phototherapy, *Int. J. Radiat. Biol.* 47, 145–147, 1985), a great deal of research has followed producing a number of phthalocyanines for photodynamic therapy. Although prior studies with phthalocyanines have been generally disappointing, primarily because of the poor solubility characteristics of the basic ring, some of these compounds have attractive characteristics.

For example, unlike some of the porphyrin compounds, phthalocyanines strongly absorb clinically useful red light with absorption peaks falling between about 600 and 810 nm (Abernathy, Chad D., Anderson, Robert E., Kooistra, Kimberly L., and Laws, Edward R., Activity of Phthalocyanine Photosensitizers against Human Glioblastoma in Vitro, *Neurosurgery*, Vol. 21, No. 4, pp. 468–473, 1987). Although porphyrins absorb light poorly in this wavelength region, as a result of the increased transparency of biological tissues at longer wavelengths, red light is normally used for photodynamic therapy. Thus, the greater absorption of red light by the phthalocyanines over porphyrins indicates deeper potential penetration with the phthalocyanines in photodynamic treatment processes.

Furthermore, it has been found that the addition of certain metal cations (i.e. diamagnetic metal cations such as aluminum) to the phthalocyanine ring will, in some instances, create a fairly stable chelate with enhanced photosensitizing tumoricidal activity. While the mechanisms for producing the photoreactions are not clear (i.e. it is not known whether singlet oxygen or hydroxyl radicals, etc. are produced), the choice of the metal cation is apparently critical in that certain metals (i.e., paramagnetic metals) may actually inhibit the phototoxic properties of the resulting compound. Abernathy, et al., pp. 470–471.

In addition, the phthalocyanines offer many benefits over the porphyrin components as photosensitizers in that the phthalocyanines are relatively easy to synthesize, purify, and characterize in contrast to the porphyrins, which are often difficult to prepare. Similarly, the metal phthalocyanines are exceptionally stable compounds in comparison to the porphyrin or porphyrin-like compounds. As a result, certain metallic phthalocyanines, such as aluminum phthalocyanine tetrasulfonate (AlPcS) and chloroaluminum phthalocyanine (AlPcCl), offer a number of advantages over porphyrins as therapeutic agents for photodynamic therapy.

However, notwithstanding some of the benefits indicated above, only a few of the many possible types of ring-substituted phthalocyanines belonging to this group have been examined. By far the most attention has been given to sulfonated phthalocyanines and to phthalocyanines with peripheral substituents carrying hydroxy, alkoxy, and amino substituents. Very little attention has been given to phthalocyanines with complex metal ligands.

The limited variety of phthalocyanines which have been tested vary greatly i their photosensitizing activity Metal-free phthalocyanines show poor photodynamic activity (Abernathy, C. D., R. E. Anderson, K. L. Kooistra, & E. R. Laws, Jr., "Activity of Phthalocyanine Photosensitizers Against Human Glioblastoma in vitro", Neurosurgery 21, pp 468–473, 1987; Chan, W. S., J. F. Marshall, G. Y. F. Lam, & I. R. Hart, "Tissue Uptake, Distribution, and Potency of the Photoactivatable Dye Chloroaluminum Sulfonated Phthalocyanine in Mice Bearing Transplantable Tumors", *Cancer Res.*) 48, pp 3040–3044, 1988, Sonoda, M., C. M. Krishna, & P. Riesz, "The Role of Singlet Oxygen in the Photohemolysis of Red Blood Cells Sensitized by Phthalocyanine Sulfonates", Photochem Photobiol. 46, pp. 625–632, 1987)

as do phthalocyanines containing paramagnetic metals. In contrast, those containing diamagnetic metals, such as Al, Sn, and Zn, are active as a result of the long half-life of the triplet state (Chan, W. S., J. F. Marshall, G. Y. F. Lam, & I. R. Hart, "Tissue Uptake, Distribution, and Potency of the Photoactivatable Dye Chloroaluminum Sulfonated Phthalocyanine in Mice Bearing Transplantable Tumors", *Cancer Res.* 48, pp. 3040–3044, 1988; Sonoda, M., C. M. Krishna, & P. Riesz, "The Role of Singlet Oxygen in the Photohemolysis of Red Blood Cells Sensitized by Phthalocyanine Sulfonates", *Photochem. Photobiol.* 46, pp. 625–632, 1987). While in general there appears to be an increase in photosensitizing ability with lipophilicity (Berg, K., J. C. Bommer, & J. Moan, "Evaluation of Sulfonated Aluminum Phthalocyanines for use in Photochemotherapy. Cellular Uptake Studies", *Cancer Letters* 44 pp. 7–15, 1989) some highly lipophilic derivatives, such as a tetraneopentoxy derivative, are poor photosensitizers (Rosenthal, I., E. Ben-Hur, S. Greenberg, A. Concepcion-Lam, D. M. Drew, & C. C. Leznoff, "The Effect of Substituents on Phthalocyanine Phototoxicity", *Photochem. Photobiol.* 46, pp. 959–963, 1987).

Recently, Leznoff, et al. (Leznoff, C. C., Vigh, S., Svirskaya, P. I., Greenberg, S., Drew, D. M., Ben-Hur, E. & Rosenthal, I., "Synthesis and Photocytoxicity of Some New Substituted Phthalocyanines", *Photochem. Photobiol.* 49, pp. 279–284, 1989) synthesized a series of ring-substituted phthalocyanines. The substituents were hydroxy or alkoxy groups, as well as substituted amines. Of this series, a Zn phthalocyanine with four diethylaminopropyl groups was reported to have some photosensitizing activity against Chinese hamster fibroblast V79 cells in culture. However, it is critical to note that although amine groups were present in the Zn phthalocyanine compound containing the four diethylaminopropyl groups, the amine groups were ring substituents and no simple axial ligands were specified. For some time the applicants have been searching for phthalocyanines having superior photosensitizing ability. In this search, the applicants have emphasized compounds with complex metal ligands. Initially, applicants examined the photocytotoxicity of twenty-one phthalocyanines taken from a collection in the applicants' laboratories to Chinese hamster fibroblasts, i.e. V79 cells. One of these phthalocyanines was $HOSiPcOSi(CH_3)_2(CH_2)_3OCH_2$—$CHOHCH_2N(C_2H_5)_2$, a phthalocyanine composition carrying a hydroxyl amine functional group. This was found to be taken up efficiently by the Chinese hamster fibroblast V79 cells and to have excellent photocytotoxicity. However, solutions of this composition in dimethylformamide were found to decompose relatively rapidly. Further, it appeared that the composition might have dark toxicity (i.e. be toxic to tissues in the absence of light) in vivo because of its —$OCHOHCH_2NR_2$ functional group.

With the results of this preliminary work in mind, the applicants then prepared and studied a series of new aluminum and silicon phthalocyanines having relatively simple ligands carrying $NR_2$ or $NR_3+$ functions. The present invention is the result of applicants' studies of these compounds, and the use of the same for photodynamic therapy.

SUMMARY OF THE INVENTION

In one aspect, the present invention is directed to a series of phthalocyanine compounds, (or compositions) with modifying moieties linked to the central metal, which is either aluminum (Al) germanium (Ge), gallium (Ga), tin (Sn), or silicon (Si). Specifically, the present invention relates to a series of aluminum, germanium, gallium, tin or silicon phthalocyanines having an axial group, or groups, carrying, or terminating in, an amine or quaternary ammonium function. The specific embodiments of the invention can be generally characterized by the following Formula I:

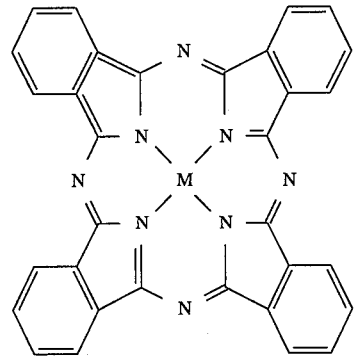

wherein M is $(G)_aY[(OSi(CH_3)_2(CH_2)_bN_c(R')_d(R'')_e)_f X_g]_p$ wherein:
Y is selected from the group of Si, Al, Ga, Ge, or Sn;
R' is selected from the group of H, C, $CH_2$, $CH_3$, $C_2H_5$, $C_4H_9$, $C_4H_8NH$, $C_4H_8N$, $C_4H_8NCH_3$,, $C_4H_8S$, $C_4H_8O$, $C_4H_8SE$, $CH_2CH_3$, $(CH_2)_3(CH_3)_2$, $OC(O)CH_3$, $OC(O)$, $(CH_3)_2(CH_2)_{11}$, CS, CO, CSE, OH, $C_4H_8N(CH_2)_3CH_3$, $(CH_2)_2N(CH_3)_2$, $C(O)C_{27}H_{30}N_2O$, $(CH_2)_nN((CH)_o(CH_3))_2$, an alkyl group having from 1 to 12 carbon atoms;
R" is selected from the group of H, $SO_2CH_3$, $(CH_2)_2N(CH_3)_2$, $(CH_2)_{11}CH_3$, $C(S)NHC_6H_{11}O_5$, $(CH_2)_nN((CH)_o(CH_3))_2$, and an alkyl group having from 1 to 12 carbon atoms;
G is selected from the group of OH, $CH_3$, and $(CH_3)_3C(CH_3)_2$;
X is selected from the group of: I; F; Cl; or Br;
$a=0$ where Y is Al, or 1 where Y is Si;
$b=$an integer from 2 to 12;
$c=0, 1$;
$d=0, 1, 2,$ or 3;
$e=0, 1,$ or 2;
$f=1$ or $2$;
$g=0, 1$;
$n=$an integer from 1 to 12;
$o=$an integer from 1 to 11;
$p=1$ or 2;

or preferably, M=
$AlOSi(CH_3)_2(CH_2)_3N(CH_3)_2$;
$AlOSi(CH_3)_2(CH_2)_3N(CH_3)_3{}^+I^-$;
$CH_3SiOSi(CH_3)_2(CH_2)_3N(CH_3)_2$;
$HOSiOSi(CH_3)_2(CH_2)_3N(CH_3)_2$;
$HOSiOSi(CH_3)_2(CH_2)_3N(CH_3)_3{}^+I^-$;
$Si[OSi(CH_3)_2(CH_2)_3N(CH_3)_3{}^+I^-]_2$;
$Si[OSi(CH_3)_2(CH_2)_4NH_2]_2$;
$Si[OSi(CH_3)_2(CH_2)_4NHSO_2CH_3]_2$;
$HOSiOSi(CH_3)_2(CH_2)_4NHSO_2CH_3$;
$HOSiOSi(CH_3)_2(CH_2)_3N(CH_2CH_3)(CH_2)_2N(CH_3)_2$;
$Si[OSi(CH_3)_2(CH_2)_4NHCSNHC_6H_{11}O_5]_2$;
$Si[OSi(CH_3)_2(CH_2)_3N(CH_3)_2]_2$;
$HOSiOSi(CH_3)_2(CH_2)_3OCOCH_3$;
$Si[OSi(CH_3)_2(CH_2)_3N^+(CH_3)_2(CH_2)_{11}CH_3]_{22I}{}^-$;
$CH_3)_3C(CH_3)_2SiOSiOSi(CH_3)_2(CH_2)_4NCOC_{27}H_{30}N_2O$;
$HOSiOSi(CH_3)_2(CH_2)_3OH$;
$Si[OSi(CH_3)_2(CH_2)_3N(CH_2CH_3)(CH_2)_2N(CH_3)_2]_2$;
$HOSiOSi(CH_3)_2(CH_2)_3NC_4H_8O$;

AlOSi(CH₃)₂(CH₂)₃N⁺(CH₃)₂(CH₂)₁₁CH₃I⁻;
HOSiOSi(CH₃)₂(CH₂)₈N(CH₃)₂;
Si[OSi(CH₃)₂(CH₂)₃NC₄H₈O]₂;
HOSiOSi(CH₃)₂(CH₂)₃NC₄H₈S;
HOSiOSi(CH₃)₂(CH₂)₃N(CH₂)₃(CH₃)₂;
HOSiOSi(CH₃)₂(CH₂)₃NCS;
HOSiOSi(CH₃)₂(CH₂)₃N[(CH₂)₃N(CH₃)₂]₂;
HOSiOSi(CH₃)₂(CH₂)₃NC₄H₈NCH₃;
Si[OSi(CH₃)₂(CH₂)₃NC₄H₈NCH₃]₂;
HOSiOSi(CH₃)₂(CH₂)₃NC₄H₈N(CH₂)₃CH₃; or
Si[OSi(CH₃)₂(CH₂)₃NC₄H₈NH]₂;

In an additional aspect, the present invention relates to the various methods of synthesizing the novel phthalocyanine compositions. The novel phthalocyanines produced by the invention exhibit enhanced characteristics which make them well suited for photodynamic therapy when utilized alone or in combination with a pharmaceutical carrier. The phthalocyanines of the present invention are also useful as immunosuppressant and to purge blood of viral components.

In a further aspect, the present invention is directed to various methods for destroying cancer tissue comprising the steps of administering to the cancer tissue an effective amount of a phthalocyanine composition having an axial group, or groups, carrying, or terminating in an amine or quaternary ammonium function, and applying light of sufficient wavelength and intensity to activate the composition thereby exerting a cell killing, or cytotoxic, effect on the cancer tissue.

BRIEF DESCRIPTION OF THE DRAWINGS

The following is a brief description of the drawings which are presented for the purpose of illustrating the invention and not for the purpose of limiting same.

DETAILED DESCRIPTION OF THE INVENTION

Figure 1:
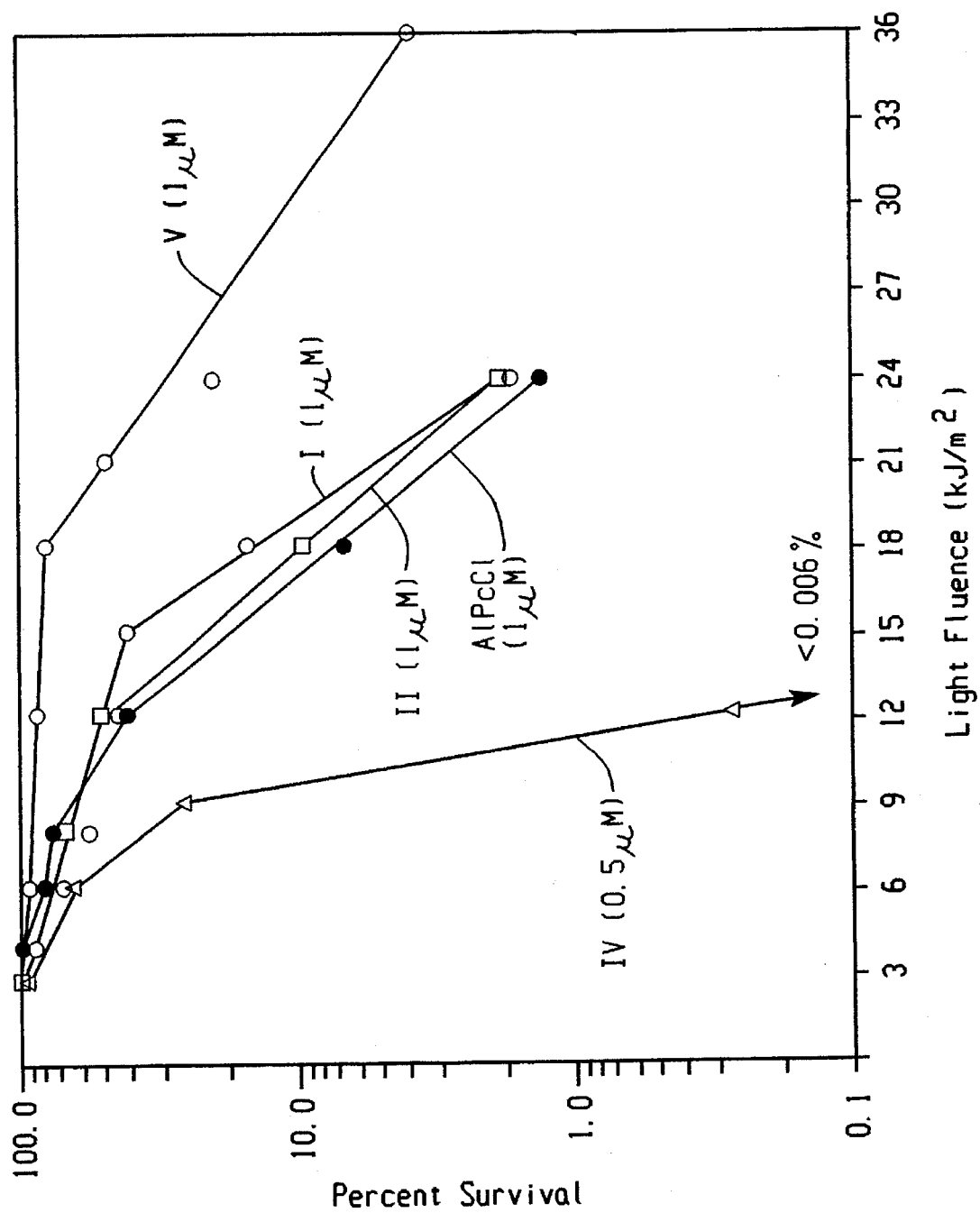
FIG. 1 is a graph illustrating the photodynamic efficacy of the various compositions of the present invention in comparison to AlPcCl. The phthalocyanine composition compounds of the present invention were tested for their photodynamic efficiency against Chinese hamster fibroblast V79 cells by colony formation. Monolayer cultures were treated with the indicated phthalocyanine composition for 18 hours, irradiated with various fluences of red light, and immediately trypsinized and replated at appropriate aliquots in triplicate. Colonies of at least 50 cells were counted after 7–10 days. The plating efficiency of the untreated cells was approximately 90%.

The present invention relates to a series of novel phthalocyanine compositions (or compounds) suitable for use as photosensitizers for photodynamic therapy. Specifically, the invention relates to a series of new aluminum (Al) or Ga and/or silicon (Si) Ge, or Sn phthalocyanines having substituted amine or quaternary ammonium axial ligands attached to the central metal, and the use of these new phthalocyanine compositions for the treatment of cancer through photosensitization. Moreover, the present invention is directed to the methods of preparing these compositions for use in photodynamic therapy.

Although research has recently been directed to the use of various phthalocyanines for photodynamic therapy, this activity has been principally directed to phthalocyanines with peripheral substituents, and little, if any, attention has been given to phthalocyanines with complex metal ligands. Along this line, in the phthalocyanine compositions described in the prior art, only simple ligands, such as Cl or OH ligands, are attached to the central metal. However, in the new compositions of the present invention, axial ligands carrying or, terminating in an amine function or a quaternary ammonium function are attached to the central metal. As a result, it is believed by the applicants that these more complex axial ligands give the new phthalocyanine compositions the potential to bind to the various species that assist in transporting the composition to and from their targets, as well as enhance the potential for the phthalocyanines to bind to their specific target cells.

This is demonstrated in that some of the novel phthalocyanines of the present invention having substituted amine or quaternary ammonium axial ligands attached to either aluminum or silicon as the central metal, are much more effective in producing photodynamic activity when compared with chloroaluminum phthalocyanine (AlPcCl). The enhanced cytotoxic effects produced are due to the increased cellular uptake of the compositions and/or the increased loss of clonogenicity as a function both of the concentration of the phthalocyanine and the red light fluence.

More particularly, in applicants' investigation for phthalocyanines exhibiting enhanced photosensitizing ability through the synthesis and evaluation of a number of phthalocyanine compositions having complex metal ligands, the applicants have produced a series of new aluminum and silicon phthalocyanines having substituted amine or quaternary axial ligands. In this regard, two silicon phthalocyanines and one aluminum phthalocyanine with axial groups terminating in an amine function were prepared:

SiPc(CH₃)(OSi(CH₃)₂(CH₂)₃N(CH₃)₂),

SiPc(OH)(OSi(CH₃)₂(CH₂)₃N(CH₃)₂), and

AlPcOSi(CH₃)₂(CH₂)₃N(CH₃)₂.

In addition, two silicon phthalocyanines and one aluminum phthalocyanine with axial groups terminating in a quaternary ammonium function were prepared:

SiPc(OH)(OSi(CH₃)₂(CH₂)₃N(CH₃)₂)⁺I⁻,

SiPc(OSi(CH₃)₂(CH₂)₃N(CH₃)₃)⁺I⁻)₂, and

AlPcOSi(CH₃)₂(CH₂)₃N(CH₃)₃⁺I⁻.

The new phthalocyanine compositions can be generally characterized by the following formula:

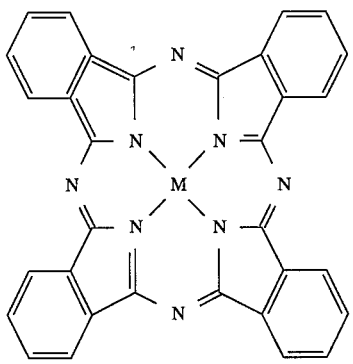

wherein M is $(G)_a Y[(OSi(CH_3)_2(CH_2)_b N_c(R')_d(R'')_e)_f X_g]_p$ wherein:

Y is selected from the group of Si, Al, Ga, Ge, or Sn;

R' is selected from the group of H, C, $CH_2$, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $CH_2CH_3$, $(CH_2)_3(CH_3)_2$, $OC(O)CH_3$, $OC(O)$, $(CH_3)_2(CH_2)_{11}$, CS, CO, CSe, OH, $C_4H_8N(CH_2)_3CH_3$, $(CH_2)_3N(CH_3)_2$, $C(O)C_{27}H_{30}N_2O$, $(CH_2)_n N((CH)_o(CH_3))_2$, an alkyl group having from 1 to 12 carbon atoms;

R'' is selected from the group of H, $SO_2CH_3$, $(CH_2)_2N(CH_3)_2$, $(CH_2)_{11}CH_3$, $C(S)NHC_6H_{11}O_5$, $(CH_2)_n N((CH)_o(CH_3))_2$, and an alkyl group having from 1 to 12 carbon atoms;

G is selected from the group of OH, $CH_3$, and $(CH_3)_3C(CH_3)_2$;

X is selected from the group of: I; F; Cl; or Br;

a=0 where Y is Al, or 1 where Y is Si;

b=an integer from 2 to 12;

c=0, 1;

d=0, 1, 2, or 3;

e=0, 1, or 2;

f=1 or 2;

g=0, 1;

n=an integer from 1 to 12;

o=an integer from 1 to 11;

p=1 or 2;

or preferably, M=
AlOSi$(CH_3)_2(CH_2)_3N(CH_3)_2$;
AlOSi$(CH_3)_2(CH_2)_3N(CH_3)_3{}^+I^-$;
$CH_3SiOSi(CH_3)_2(CH_2)_3N(CH_3)_2$;
HOSiOSi$(CH_3)_2(CH_2)_3N(CH_3)_2$;
HOSiOSi$(CH_3)_2(CH_2)_3N(CH_3)_3{}^+I^-$;
Si$[OSi(CH_3)_2(CH_2)_3N(CH_3)_3{}^+I^-]_2$;
Si$[OSi(CH_3)_2(CH_2)_4NH_2]_2$;
Si$[OSi(CH_3)_2(CH_2)_4NHSO_2CH_3]_2$;
HOSiOSi$(CH_3)_2(CH_2)_4NHSO_2CH_3$;
HOSiOSi$(CH_3)_2(CH_2)_3N(CH_2CH_3)(CH_2)_2N(CH_3)_2$;
Si$[OSi(CH_3)_2(CH_2)_4NHCSNHC_6H_{11}O_5]_2$;
Si$[OSi(CH_3)_2(CH_2)_3N(CH_3)_2]_2$;
HOSiOSi$(CH_3)_2(CH_2)_3OCOCH_3$;
Si$[OSi(CH_3)_2(CH_2)_3N^+(CH_3)_2(CH_2)_{11}CH_3]_2 2I^-$;
$(CH_3)_3C(CH_3)_2SiOSiOSi(CH_3)_2(CH_2)_4NCOC_{27}H_{30}N_2O$;
HOSiOSi$(CH_3)_2(CH_2)_3OH$;
Si$[OSi(CH_3)_2(CH_2)_3N(CH_2CH_3)(CH_2)_2N(CH_3)_2]_2$;
HOSiOSi$(CH_3)_2(CH_2)_3NC_4H_8O$;
AlOSi$(CH_3)_2(CH_2)_3N^+(CH_3)_2(CH_2)_{11}CH_3 I^-$;
HOSiOSi$(CH_3)_2(CH_2)_8N(CH_3)_2$;
Si$[OSi(CH_3)_2(CH_2)_3NC_4H_8O]_2$;
HOSiOSi$(CH_3)_2(CH_2)_3NC_4H_8S$;
HOSiOSi$(CH_3)_2(CH_2)_3N(CH_2)_3(CH_3)_2$;
HOSiOSi$(CH_3)_2(CH_2)_3NCS$;
HOSiOSi$(CH_3)_2(CH_2)_3N[(CH_2)_3N(CH_3)_2]_2$;
HOSiOSi$(CH_3)_2(CH_2)_3NC_4H_8NCH_3$;
Si$[OSi(CH_3)_2(CH_2)_3NC_4H_8NCH_3]_2$;
HOSiOSi$(CH_3)_2(CH_2)_3NC_4H_8N(CH_2)_3CH_3$; or
Si$[OSi(CH_3)_2(CH_2)_3NC_4H_8NH]_2$.

The new phthalocyanine compositions bearing the substituted amine or quaternary ammonium axial ligands have been evaluated for their photodynamic efficiency against Chinese hamster fibroblast V79 cells in vitro. Chloroaluminum phthalocyanine (AlPcCl) was used as a reference compound. Along this line, the compounds, SiPc$(CH_3)(OSi(CH_3)_2(CH_2)_3N(CH_3)_2)$ and SiPc$((OSi(CH_3)_2(CH_2)_3N(CH_3)_3{}^+I^-)_2$, displayed less effective cellular uptake, and are less preferred. The most efficient photosensitizer, as judged by uptake, growth delay, and photocytotoxicity, was SiPc$(OH)(OSi(CH_3)_2(CH_2)_3N(CH_3)_2)$. The related quaternary ammonium compound, SiPc$(OH)OSi(CH_3)_2(CH_2)_3N(CH_3)_3{}^+I^-)$, displayed poorer uptake but induced marked photocytotoxicity. When expressed as a function of the product of intracellular phthalocyanine and the fluence reducing cell survival to 10%, this quaternary ammonium compound was the most efficient photosensitizer.

The specific process utilized to synthesize the aluminum and silicon phthalocyanine compounds of the present invention, and the enhanced results produced through the use of these new compounds for photodynamic therapy, are more particularly described below in the following examples.

EXAMPLES

Synthesis of Phthalocyanines $CH_3OSi(CH_3)_2(CH_2)_3N(CH_3)_2$—Under argon gas a solution of $CH_3MgCl$ in tetrahydrofuran (3.0M, 45 mL) was added dropwise to a cool (ice bath) solution of $(CH_3O)_3Si(CH_2)_3N(CH_3)_2$ (11 mL) in tetrahydrofuran (100 mL), and the resulting suspension was stirred for 2 hours while being kept cool at about 5° C.). Methanol (20 mL) then was added to the suspension and the mixture formed was filtered. The solid was washed with ether (50 mL) and the washings and filtrate were combined and concentrated with a rotary evaporator (45° C.). The concentrate was fractionally distilled under vacuum (45 torr) and a selected fraction (86°–88° C., 5.0 g.) was retained (55%): NMR (CDCl$_3$) δ3.42 (s, $CH_3O$), 2.24 (m, γ-$CH_2$), 2.20 (s, $NCH_3$), 1.49 (m, β-$CH_2$), 0.57 (m, α-$CH_2$), 0.10 (s, $CH_3Si$). The compound is a colorless liquid.

AlPcOSi$(CH_3)_2(CH_2)_3N(CH_3)_2$—Compound I. A mixture of $CH_3OSi(CH_3)_2(CH_2)_3N(CH_3)_2$ (203 mg) produced above and a suspension of AlPcOh xH$_2$O (56 mg) and 2-ethylpyridine (15 mL) that had been dried by distillation (3 mL of distillate) was refluxed for 45 minutes and filtered. The filtrate was evaporated to dryness with a rotary evaporator (~40° C.) and the solid was dissolved CH$_2$Cl$_2$ (2 mL). Hexanes (3 mL) were added to the solution and the resulting suspension was filtered. The solid was washed (benzene and hexanes), vacuum dried (65° C.), and weighed (63 mg, 98% assuming AlPcOH 3H$_2$O); NMR (C$_5$D$_5$N, 70° C.) δ9.65 (m, 1,4-PcH), 8.28 (m, 2,3-PcH), 1.63 (s, $NCH_3$), 0.99 (m, γ-$CH_2$), –0.50 (m, β-$CH_2$), –1.80 (m, α-$CH_2$), –2.33 (s, SiCH$_3$).

The compound is blue and is soluble in $CH_2Cl_2$ and toluene.

AlPcOSi$(CH_3)_2(CH_2)_3N(CH_3)_3{}^+I^-$—Compound II. A mixture of AlPcOSi$(CH_3)_2(CH_2)_3N(CH_3)_2$ (30 mg), benzene (10 mL), and $CH_3I$ (15 μL) was refluxed for 1.5 hours, cooled, and filtered. The solid was vacuum dried (60° C.) and weighed (31 mg., 86%): NMR ($C_5D_5N$, 70° C.) δ9.75 (m, 1,4-PcH), 8.34 (m, 2,3-PcH), 2.90 (s, $NCH_3$), 2.02 (m, γ-$CH_2$), −0.53 (m, β-$CH_2$), −1.87 (m, α$CH_2$), −2.40 (s, $SiCH_3$).

The compound is a blue solid and is soluble in $CH_2Cl_2$ and $CH_3OH$ but is insoluble in toluene and $H_2O$.

$CH_3SiPcOSi(CH_3)_2(CH_2)_3N(CH_3)_2$—Compound III. Procedures in this synthesis that were carried out under low light conditions (room lights off, shades drawn) are identified by the symbol 1. A mixture of $CH_3OSi(CH_3)_2(CH_2)_3N(CH_3)_2$ (224 mg) and a suspension of $CH_3SiPcOH$ (117 mg) and pyridine (25 mL) that had been dried by distillation (1) was slowly distilled (1) for 3 hours (10 mL of distillate) and then filtered (1, no solid). The filtrate was evaporated to dryness with a rotary evaporator (1, 75° C.), and the solid was dissolved in $CH_2Cl_2$ (1, 2 mL). Hexanes (30 mL) were added to the solution (1) and the resulting suspension was filtered (1). The solid was washed (hexanes), vacuum dried (65° C.), and weighed (11 mg, 76%): mp >260° C.; NMR ($CDCl_3$) δ9.63 (m, 1,4-PcH), 8.33 (m, 2,3-PcH), 1.74 (s, $NCH_3$), 1.01 (m, γ-$CH_2$), −1.18 (m, β-$CH_2$), −2.25 (m, α-$CH_2$), −2.96 (s, $Si(CH_3)_2$), −6.35 (s, $SiCH_3$).

The compound is dark green and is soluble in $CH_2Cl_2$ and toluene. Solutions of it are rapidly photolyzed by white light.

$HOSiPcOSi(CH_3)_2(CH_2)_3N(_3)_2$—Compound I. A mixture of $CH_3SiPcOSi(CH_3)_2(CH_2)_3N(CH_3)_2$ (35 mg), $N(C_2H_5)_3$ saturated with $H_2O$ (0.2 mL), and toluene (70 mL) was irradiated with an incandescent light (300 W in 35 mm slide projector) for 15 minutes. The resulting suspension was concentrated with a rotary evaporator (~45° C.) and the concentrate (~5 mL) was diluted with hexanes (1 mL). The suspension formed was filtered and the solid was washed (hexanes), vacuum dried (65° C.), and weighed (33 mg, 96%): mp>260° C.; NMR (dimethylformamide-$d_7$, 70° C.) δ9.68 (m, 1,4-PcH), 8.47 (m, 2,3-PcH), 1.52 (s, $NCH_3$), 0.74 (m, γ-$CH_2$), −1.11 (m, β-$CH_2$), −2.27 (m, α-$CH_2$), −2.89 (s, $SiCH_3$). MS-HRFAB exact mass m/z calculated for $C_{39}H_{35}N_9O_2Si_2$M+7.17.2452. Found 717.2422.

The compound is blue and is soluble in $CH_2Cl_2$ and toluene.

$HOSiPcOSi(CH_3)_2(CH_2)_3N(CH_3)_3^+I^-$—Compound V. A mixture of $HOSiPcOSi(CH_3)_2(CH_2)_3N(CH_3)_2$ (24 mg), $CH_3I$ (25 μL), and benzene (10 mL) was refluxed for 1.5 hours, cooled, and filtered. The solid was washed (benzene), vacuum dried (65° C.), and weighed (23 mg, 81%): NMR (dimethylformamide-$d_7$, 70° C.) δ9.66 (m, 1,4-PcH), 8.45 (m, 2,3-PcH), 2.87 (s, $NCH_3$), 2.06 (m, γ-$CH_2$), −0.97 (m, β-$CH_2$), 2.25 (m, α-$CH_2$), −2.83 (s, $SiCH_3$). MS-HRFAB exact m/z calculated for $C_{40}H_{38}N_9O_2Si_2$ (M-I)$^+$ 732.2687. Found 732.2668.

The compound is blue. It is soluble in $CH_2Cl_2$ and $CH_3OH$ but is insoluble in toluene and $H_2O$.

$Sipc[OSi(CH_3)_2(CH_2)_3N(CH_3)_2]_2$. A mixture of $CH_3OSi(CH_3)_2(CH_2)_3N(CH_3)_2$ (239 mg) and a suspension of $SiPc(OH)_2$ (232 mg) and 2-ethylpyridine (30 mL) that had been dried by distillation (~2 mL of distillate) was slowly distilled for 2 hours (~5 mL of distillate). The resulting solution was filtered, the filtrate was evaporated to dryness with a rotary evaporator (~60° C.), and the solid was dissolved in $CH_2Cl_2$ (3.5 mL). The $CH_2Cl_2$ solution was diluted with hexanes (~40 mL), the suspension formed was filtered, and the solid was washed (hexanes), air dried, and weighed (263 mg, 76%); NMR ($CDCl_3$), δ9.63 (m, 1,4-PcH), 8.34 (m, 2,3-PcH), 1.65 (s, $NCH_3$), 0.90 (m, γ-$CH_2$), −1.10 (m, β-$CH_2$), −2.26 (m, α-$CH_2$), −2.87 (s, $SiCH_3$).

The compound is blue and is soluble in $CH_2Cl_2$ and toluene.

$SiPc[OSi(CH_3)_2(CH_2)_3N(CH_3)_3)^+I^-]_2$—Compound VI. A mixture of $SiPc[OSi(CH_3)_2(CH_2)_3N(CH_3)_2]_2$ produced above (30 mg), $CH_3I$ (36 μL) and benzene (5 mL) was refluxed for 1.5 hours, cooled, and filtered. The solid was washed (benzene, hexanes), vacuum dried (60° C.), and weighed (32 mg, 79%): NMR ($CD_3OD$) δ9.63 (m, 1.4-PcH), 8.41 (m, 2,3-PcH), 1.65 (s, $NCH_3$), 0.90 (m, γ-$CH_2$), −1.10 (m, β-$CH_2$), −2.21 (m, α-$CH_2$), −2.90 (m, $SiCH_3$).

The compound is blue and is soluble in $CH_2Cl_2$ and $CH_3OH$ but is insoluble in toluene. It disperses in $H_2O$ but doses not dissolve in it.

Additional Phthalocyanine Compounds $SiPc[OSi(CH_3)_2(CH_2)_4NH_2]_2$ Compound VII A mixture of $CH_3OSi(CH_3)_2(CH_2)_4NH_2$ (100 μL, 0.53 mmol), $SiPC(OH)_2$ (65 mg, 0.11 mmol) and pyridine (15 ml) was distilled for 30 minutes (~5 ml distillate) and filtered. The filtrate was evaporated to dryness with a rotary evaporator (~70° C.). The solid was dissolved in ethanol (4 ml), precipitated from the solution with water (3 ml), recovered by filtration, washed (ethanol-water solution, 2:1), vacuum dried (~60° C.) and weighed (81 mg, 0.097 mmol, 88%): UV-Vis (toluene) $\lambda_{max}$ 669 nm; NMR ($CDCl_3$) δ9.67 (m, 1,4-Pc H), 8.36 (m, 2,3-Pc H), 1.71 (t, δ-$CH_2$), −0.10 (m, γ-$CH_2$), −1.33 (m, β-$CH_2$), −2.20 (m, α-$CH_2$), −2.87 (s, $SiCH_3$). MS-HRFAB exact mass, m/z: calculated for $C_{44}H_{48}N_{10}O_2Si_3$ (M)$^+$, 832.3270; found, 832.3261, 832.3274. The compound is blue and is soluble in $CH_2Cl_2$, dimethylformamide, pyridine and ethanol.

$HOSiPcOSi(CH_3)_2(CH_2)_3N(CH_2CH_3)(CH_2)_2N(CH_3)_2$ Compound X

To prepare $CH_3OSi(CH_3)_2(CH_2)_3N(CH_2CH_3)(CH_2)_2N(CH_3)_2$, a solution of $CH_3OSi(CH_3)_2(CH_2)_3Cl$ (5.06 g, 30 mmol), $CH_3CH_2NH(CH_2)_2N(CH_3)_2$ (5.0 mL, 61 mmol) and $CH_3OH$ (5.0 ml) was refluxed for 6 hours and then distilled under gradually reduced pressure (20 torr final). The remainder was diluted with ether (20 ml) and filtered. The solid was washed (ether) and the washings and the filtrate were combined and concentrated with a rotary evaporator (~25° C.). The concentrate was fractionally distilled under vacuum (7 mtorr) and a selected fraction (30°–35° C.) was retained (432 mg, 1.8 mmol, 6%): NMR ($CDCl_3$) δ3.40 (s, $CH_3O$), 2.53 (m, $NCH_2CH_3$ and $CH_2CH_2NCH_3$), 2.37 (m, γ-$CH_2$ and $CH_2CH_2NCH_3$), 2.21 (s, $NCH_3$), 1.46 (m, β-$CH_2$), 0.97 (t, $NCH_2CH_3$), 0.52 (m, α-$CH_2$), 0.07 (s, $SiCH_3$). The compound is a colorless oil.

All steps but the finally drying step of this procedure were carried out under low-intensity illumination. To prepare $CH_3SiPcOSi(CH_3)_2(CH_2)_3N(CH_2CH_3)(CH_2)_2N(CH_3)_2$, a mixture of the $CH_3OSi(CH_3)_2(CH_2)_3N(CH_2CH_3)(CH_2)_2N(CH_3)_2$ (432 mg, 1.8 mmol) and a suspension of $CH_3SiPcOH$ (291 mg, 0.51 mmol) and pyridine (120 ml) that had been dried by distillation (~23 ml of distillate) was slowly distilled for 3 hours (~5 ml of distillate) and then filtered. The filtrate was evaporated to dryness with a rotary evaporator (~80° C.). The solid was dissolved in $CH_2Cl_2$ (1 ml), precipitated from the solution with hexanes (20 ml), recovered by filtration, washed ($CH_3OH$ and hexanes), vacuum dried (~90° C.) and weighed (306 mg, 0.39 mmol, 76%): NMR ($CD_2Cl_2$) δ6 9.68 (m, 1,4-Pc H), 8.40 (m, 2,3-Pc H), 2.01 (s, $NCH_3$), 1.85 (s, $NCH_2CH_2N$), 1.83 (q, $NCH_2CH_3$), 0.98 (m, γ-$CH_2$), 0.61

(t, NCH$_2$CH$_3$), −1.18 (m, β-CH$_2$), −2.39 (m, α-CH$_2$), −2.94 (s, Si(CH$_3$)$_2$), −6.33 (s, SiPcCH$_3$). The compound is green and is soluble in CH$_2$Cl$_2$ and toluene. Solutions of it are rapidly photolyzed by white light.

To prepare HOSiPcOSi(CH$_3$)$_2$(CH$_2$)$_3$N(CH$_2$CH$_3$)(CH$_2$)$_2$N(CH$_3$)$_2$, a mixture of the CH$_3$SiPcOSi(CH$_3$)$_2$(CH$_2$)$_3$N(CH$_2$CH$_3$)(CH$_2$)$_2$N(CH$_3$)$_2$ (300 mg, 0.38 mmol), toluene (600 ml) and (C$_2$H$_5$)$_3$N saturated with H$_2$O (2.2 ml) was irradiated with incandescent light (300 W projector lamp) for 40 minutes, and then concentrated with a rotary evaporator (~70° C.). The concentrate (~5 ml) was diluted with hexanes (2.5 ml) and filtered. The solid was washed (toluene), dissolved in CH$_2$Cl$_2$ (2 ml), precipitated from the solution with hexanes (20 ml), recovered by filtration, was washed (hexanes), vacuum dried (~90° C.), and weighed (136 mg, 0.17 mmol, 45%): UV-vis (toluene) $\lambda_{max}$ 670 nm; NMR (CD$_2$Cl$_2$, 7.6 mM) δ9.28 (m, 1,4-Pc H), 8.30 (m, 2,3-Pc H), 1.93 (s, NCH$_3$), 1.77 (s, NCH$_2$CH$_2$N), 1.71 (q, NCH$_2$CH$_3$), 0.85 (m, γ-CH$_2$), 0.49 (t, NCH$_2$CH$_3$), −1.24 (m, β-CH$_2$), −2.43 (m, α-CH$_2$), −3.02 (s, SiCH$_3$). Anal. calculated for C$_{43}$H$_{44}$N$_{10}$O$_2$Si$_2$: C,65.45; H,5.62; N,17.75. Found: C,65.18; H,5.51; N,17.74. The compound is blue. It is soluble in toluene, CH$_2$Cl$_2$, dimethylformamide and ethanol.

SiPc[OSi(CH$_3$)$_2$(CH$_2$)$_3$N(CH$_3$)$_2$]$_2$ Compound XII

A mixture of CH$_3$OSi(CH$_3$)$_2$(CH$_2$)$_3$N(CH$_3$)$_2$ (201 mg, 1.1 mmol) and a suspension of SiPc(OH)$_2$ (232 mg, 0.40 mmol) and 2-ethylpyridine (30 ml) that had been dried by distillation (~1 ml of distillate) was slowly distilled for 1.5 hours (~11 ml of distillate). The resulting solution was filtered, and the filtrate was evaporated to dryness with a rotary evaporator (~40° C.). The sol id formed was extracted (CH$_2$Cl$_2$-hexanes solution, 1:4, 15 ml), recovered from the extract by rotary evaporation (~40° C.), dissolved in CH$_2$Cl$_2$ (1.5 ml), precipitated from the solution with hexanes (18 ml), recovered by filtration, washed (hexanes), vacuum dried (~70° C.) and weighed (110 mg, 0.13 mmol, 33%): UV-vis (toluene) $\lambda_{max}$ 669 nm; NMR (CDCl$_3$) δ9.61 (m, 1,4-Pc H), 8.31 (m, 2,3-Pc H), 1.55 (s, NCH$_3$), 0.80 (m, γ-CH$_2$), −1.14 (m, β-CH$_2$), −2.29 (m, α-CH$_2$), −2.89 (s, SiCH$_3$). MS-HRFAB exact mass, m/z: calculated for C$_{46}$H$_{53}$N$_{10}$O$_2$Si$_3$ (M+H)$^+$, 861.3661; found, 861.3627, 861.3638. The compound is blue and is soluble in CH$_2$Cl$_2$, dimethylformamide and toluene.

SiPc[OSi(CH$_3$)$_2$(CH$_2$)$_3$N(CH$_2$CH$_3$)(CH$_2$)$_2$N(CH$_3$)$_2$]$_2$ Compound XVIII A mixture of CH$_3$OSi(CH$_3$)$_2$(CH$_2$)$_3$N(CH$_2$CH$_3$)(CH$_2$)$_2$N(CH$_3$)$_2$ (191 mg, 0.77 mmol) and a suspension of SiPc(OH)$_2$ (144 mg, 0.25 mmol) and pyridine (45 ml) that had been dried by distillation (~9 ml of distillate) was slowly distilled for 1 hours (~3 ml of distillate) and then filtered. The filtrate was evaporated to dryness with a rotary evaporator (~80° C.), and the solid was extracted (CH$_2$Cl$_2$, 10 ml), recovered from the extract by rotary evaporation (~40° C.), washed twice (ethanol-water solution, 1:4), vacuum dried (~90° C.) and weighed (123 mg, 0.12 mmol, 48%): UV-vis (toluene) $\lambda_{max}$ 668 nm; NMR (CDCl$_3$) δ9.64 (m, 1,4-Pc H), 8.33 (m, 2,3-Pc H), 2.03 (s, NCH$_3$), 1.91 (s, NCH$_2$CH$_2$N), 1.84 (q, NCH$_2$CH$_3$), 1.04 (m, γ-CH$_2$), 0.64 (t, NCH$_2$CH$_3$), −1.14 (m, γ-CH$_2$), −2.39 (m, α-CH$_2$), −2.89 (s, SiCH$_3$ ). MS-HRFAB exact mass, m/z: calculated for C$_{54}$H$_{70}$N$_{12}$O$_2$Si$_3$ (M+H)$^+$, 1003.5131; found, 1003.5085, 1003.5100. The compound is blue and is soluble in CH$_2$Cl$_2$, dimethylformamide and toluene.

HOSiPcOSi(CH$_3$)$_2$(CH$_2$)$_3$N[(CH$_2$)$_3$N(CH$_3$)$_2$]$_2$ Compound XXVIII To prepare CH$_3$OSi(CH$_3$)$_2$(CH$_2$)$_3$N[(CH$_2$)$_3$N(CH$_3$)$_2$]$_2$, a mixture of CH$_3$OSi(CH$_3$)$_2$(CH$_2$)$_3$Cl (3.05 g, 18 mmol), NH[(CH$_2$)$_3$N(CH$_3$)$_2$]$_2$ (8.0 mL, 36 mmol), K$_2$CO$_3$ (0.488 g, 3.5 mmol) and CH$_3$OH (1.0 ml) was heated in oil bath (~110° C.) for 48 hours and filtered. The filtrate was fractionally distilled under vacuum (5 mtorr) and a selected fraction (99°–102° C.), was retained (543 mg): NMR (CDCl$_3$) δ3.40 (s, CH$_3$O), 2.33 (m, CH$_2$CH$_2$CH$_2$NCH$_3$), 2.19 (s, NCH$_3$), 1.61 (quintet, CH$_2$CH$_2$CH$_2$NCH$_3$), 1.43 (m, β-CH$_2$), 0.55 (m, α-CH$_2$), 0.07 (s, SiCH$_3$). The product is a yellow oil.

All steps but the finally drying step of this procedure were carried out under low-intensity illumination . To prepare CH$_3$SiPcOSi(CH$_3$)$_2$(CH$_2$)$_3$N[(CH$_2$)$_3$N(CH$_3$)$_2$]$_2$, a mixture of the crude CH$_3$OSi(CH$_3$)$_2$(CH$_2$)$_3$N](CH$_2$)$_3$N(CH$_3$)$_2$]$_2$ (322 mg) and a suspension of CH$_3$SiPcOH (302 mg, 0.53 mmol) and pyridine (170 ml) that had been dried by distillation (~23 ml of distillate) was slowly distilled for 3 hours (~20 ml of distillate) and then filtered. The filtrate was evaporated to dryness with a rotary evaporator (~80° C.). The solid was washed (ethanol-water solution, 1:2) and chromatographed (Al$_2$O$_3$V, 3.5×15 cm, ethyl acetate-CH$_3$OH solution, 9:1) and the resulting solid was vacuum dried (~60° C.) and weighed (194 mg, 0.23 mmol, 43%): NMR (CDCl$_3$) δ9.60 (m, 1,4-Pc H), 8.29 (m, 2,3-Pc H), 2.08 (s, NCH$_3$), 1.96 (t, CH$_2$CH$_2$CH$_2$NCH$_3$), 1.73 (t, CH$_2$CH$_2$CH$_2$NCH$_3$), 1.11 (quintet, CH$_2$CH$_2$CH$_2$NCH$_3$), 0.96 (m, γ-CH$_2$), −1.18 (m, β-CH$_2$), −2.46 (m, α-CH$_2$), −2.98 (s, Si(CH$_3$)$_2$), −6.39 (s, SiPcCH$_3$). The compound is green and is soluble in CH$_2$Cl$_2$ and toluene. Solutions of it are rapidly photolyzed by white light.

(Pc 27). A mixture of CH$_3$SiPcOSi(CH$_3$)$_2$(CH$_2$)$_3$N[(CH$_2$)$_3$N(CH$_3$)$_2$]$_2$ (180 mg, 0.21 mmol), toluene (360 ml), (C$_2$H$_5$)$_3$N (18 ml) and H$_2$O (1.5 ml) was irradiated with incandescent light (300 W projector lamp) for 25 minutes and then evaporated to dryness with a rotary evaporator (~35° C.). The solid was chromatographed (Al$_2$O$_3$ V, 3×14 cm, ethyl acetate-CH$_3$OH solution, 9: 1) and the resulting solid was dissolved in CH$_2$Cl$_2$ (2 ml), precipitated from the solution with pentane (12 ml ), recovered by filtration, washed (CH$_2$Cl$_2$-pentane solution, 1:6; pentane), vacuum dried (~60° C.) and weighed (74.3 mg, 0.086 mmol, 41%): UV-vis (dimethylformamide) $\lambda_{max}$ 668 nm; NMR (CD$_2$Cl$_2$, 6.7 mM) δ9.14 (m, 1,4-Pc H), 8.12 (m, 2,3-Pc H), 1.84 (s, NCH$_3$), 1.71 (t, NCH$_2$CH$_2$CH$_2$NCH$_3$), 1.47 (t, CH$_2$CH$_2$CH$_2$NCH$_3$), 0.83 (quintet, CH$_2$CH$_2$CH$_2$NCH$_3$), 0.64 (m, γ-CH$_2$), −1.41 (m, β-CH$_2$), −2.61 (m, α-CH$_2$), −3.17 (s, SiCH$_3$). MS-HRFAB exact mass, m/z: calculated for C$_{47}$H$_{53}$N$_{11}$O$_2$Si$_2$ (M+H)$^+$, 860.4001; found, 860.4020, 860.4011. The compound is blue and is soluble in CH$_2$Cl$_2$, dimethylformamide and toluene.

HOSiPcOSi(CH$_3$)$_2$(CH$_2$)$_3$NC$_4$H$_8$NCH$_3$ Compound XXVIII

To prepare CH$_3$OSi(CH$_3$)$_2$(CH$_2$)$_3$NC$_4$H$_8$NCH$_3$, a solution of CH$_3$OSi(CH$_3$)$_2$(CH$_2$)$_3$Cl (3.09 g, 19 mmol), HNC$_4$H$_8$N(CH$_3$) (4.0 mL, 36 mmol) and CH$_3$OH (1.0 ml) was heated in an oil bath (~110° C.) for 22 hours and allowed to stand for 8 h. The resultant was decanted and the upper layer was retained (2.40 g): NMR (CDCl$_3$) δ3.40 (s, CH$_3$O), 2.45 (m, NCH$_2$CH$_2$N), 2.32 (m, γ-CH$_2$), 2.26 (s, NCH$_3$), 1.51 (m, β-CH$_2$), 0.55 (m, α-CH$_2$), 0.08 (s, SiCH$_3$). The product is a yellow oil.

All steps but the finally drying step of this procedure were carried out under low-intensity illumination. To prepare CH$_3$SiPcOSi(CH$_3$)$_2$(CH$_2$)$_3$NC$_4$H$_8$NCH$_3$A mixture of the crude CH$_3$OSi(CH$_3$)$_2$(CH$_2$)$_3$NC$_4$H$_8$NCH$_3$ (162 mg) and a suspension of $CH_3SiPcOH$ (201 mg, 0.35 mmol) and pyridine (90 ml) that had been dried by distillation (~9 ml of distillate) was slowly distilled for 3 hours (~10 ml of distillate) and then filtered. The filtrate was evaporated to dryness with a rotary evaporator (~80° C.). The solid was washed (ethanol-water solution, 1:4), vacuum dried (~60° C.) and weighed (252 mg, 0.33 mmol, 94%): NMR (7.3 mM, $CDCl_3$) δ9.61 (m, 1,4-Pc H), 8.31 (m, 2,3-Pc H), 2.25 (s, $NCH_3$), 1.65 (m, $NCH_2CH_2N$), 0.90 (m, γ-$CH_2$), −1.25 (m, β-$CH_2$), −2.38 (m, α-$CH_2$), −2.98 (s, $Si(CH_3)_2$), −6.38 (s, $SiPcCH_3$). The compound is green and is soluble in $CH_2Cl_2$ and toluene. Solutions of it are rapidly photolyzed by white light.

A mixture of the $CH_3SiPcOSi(CH_3)_2(CH_2)_3NC_4H_8NCH_3$ (200 mg, 0.26 mmol), toluene (400 ml), $(C_2H_5)_3N$ (4.0 ml) and $H_2O$ (1.0 ml) was irradiated with incandescent light (300 W projector lamp) for 20 minutes, and then concentrated with a rotary evaporator (~70° C.). The concentrate (~5 ml) was diluted with hexanes (3.0 ml) and filtered. The solid was washed (toluene), dissolved in $CH_2Cl_2$ (6 ml), precipitated from the solution with hexanes (12 ml), recovered by filtration, washed (hexanes), vacuum dried (~60° C.), and weighed (82.9 mg, 0.11 mmol, 42%): UV-vis (dimethylformamide) $\lambda$max 668 nm; NMR ($CDCl_3$, 7.8 mM) δ9.15 (m, 1,4-Pc H), 8.18 (m, 2,3-Pc H), 2.16 (s, $NCH_3$), 1.61 (m, $NCH_2CH_2N$), 0.76 (m, γ-$CH_2$), −1.37 (m, β-$CH_2$), −2.49 (m, α-$CH_2$), −3.10 (s, $SiCH_3$). MS-HRFAB exact mass, m/z: calculated for $C_{42}H_{40}N_{10}O_2Si_2$ $(M+H)^+$, 773.2953; found, 773.2944, 773.2950. The compound is blue and is soluble in $CH_2Cl_2$, dimethylformamide and toluene.

The following compounds were made in a fashion similar to that used for the above compounds.

$SiPc[OSi(CH_3)_2(CH_2)_4NHSO_2CH_3]_2$ Compound VIII A solution of $CH_3SO_2Cl$, $SiPc[OSi(CH_3)_2(CH_2)_4NH_2]_2$, $(C_2H_5)_3N$ and $CH_2Cl_2$ was stirred, and the product was isolated, chromatographed and recrystallized: MS-HRFAB exact mass, m/z: calculated for $C_{46}H_{52}N_{10}O_6S_2Si_2$ $(M)^+$, 988.2821; found, 988.2817, 988.2777.

$HOSiPCOSi(CH_3)_2(CH_2)_4NHSO_2CH_3$ Compound IX A mixture of $CH_3OSi(CH_3)_2$ $(CH_2)_4NH_2$, $CH_3SiPcOH$ and pyridine was partially distilled and the resulting $CH_3SiPcOSi(CH_3)_2(CH_2)_4NH_2$ was isolated and recrystallized. A solution of this compound, $CH_3SO_2Cl$, $(C_2H_5)_3N$ and $CH_2Cl_2$ was stirred and the $CH_3SiPcOSi(CH_3)_2(CH_2)_4NHSO_2CH_3$ formed was isolated and chromatographed. Finally, a mixture of this intermediate, $CH_2Cl_2$, $H_2O$ and $(C_2H_5)_3N$ was irradiated with light and the product was isolated, chromatographed and recrystallized: MS-HRFAB exact mass, m/z: calculated for $C_{39}H_{35}N_9O_4SSi_2$ $(M)^+$, 781.2071; found, 781.2049, 781.2074.

$SiPc[OSi(CH_3)_2(CH_2)_4NHCSNHC_6H_{11}, _{O5}]_2$ Compound XI A mixture of 2,3,4,6-tetra-O-acetyl-β-D-glucopyranosyl isothiocyanate, $SiPc[OSi(CH_3)_2(CH_2)_4NH_2]_2$ and benzene was refluxed and the resulting SiPc $[OSi(CH_3)_2(CH_2)_4NHCSNHC_{14}H_{19}O_9]_2$ was isolated. A solution of this compound and $CH_3OH$ was treated with $NH_3$ gas and the product was isolated and recrystallized: MS-HRFAB exact mass, m/z: calculated for $C_{58}H_{70}N_{12}O_{12}S_2Si_3$ $(M)^+$, 1274.3986; found, 1274.3988, 1274.4024.

$HOSiPcOSi(CH_3)_2(CH_2)_3OCOCH_3$ Compound XIII A mixture of $ClSi(CH_3)_2(CH_2)_3OCOCH_3$, $CH_3SiPcOH$ and pyridine was refluxed, and the resulting $CH_3SiPcOSi(CH_3)_2(CH_2)_3OCOCH_3$ was isolated A solution of this compound and toluene was irradiated with light and the product was isolated and recrystallized: MS-HRFAB exact mass, m/z: calculated for $C_{39}H_{32}N_8O_4Si_2$ $(M)^+$, 732.2085; found, 732.2100, 732.2084

$SiPc[OSi(CH_3)_2(CH_2)_3N^+(CH_3)_2(CH_2)_{11}CH_3]_2$ $2I^-$ Compound XIV A solution of $CH_3(CH_2)_{11}I$, $SiPcOSi(CH_3)_2(CH_2)_3N(CH_3)_2$ and tetrahydrofuran was refluxed, and the product was isolated and recrystallized. Anal. calculated for $C_{70}H_{102}I_2N_{10}O_2Si_3$: C,57.84; H,7.07; I,17.46; N,9.64. Found: C,58.19; H,6.52; I,17.40; N,9.04, 9.63, 9.63.

$(CH_3)_3C(CH_3)_2SiOSiPcOSi(CH_3)_2(CH_2)_4NCOC_{27}H_{30}N_2O$ Compound XV A solution of $CH_3OSi(CH_3)_2(CH_2)_4NH_2$, $(CH_3)_3C(CH_3)_2SiOSiPcOH$ and pyridine was partially distilled and the resulting $(CH_3)_3C(CH_3)_2SiOSiPcOSi(CH_3)_2(CH_2)_4NH_2$ was isolated A solution of this compound and $CH_2Cl_2$ was mixed with a mixture of rhodamine B base, $(COCl)_2$ and benzene which had been partially distilled, and the product was isolated and chromatographed: MS-HRFAB exact mass, m/z: calculated for $C_{72}H_{75}N_{11}O_4Si_3$ $(M)^+$, 1241.5311; found 1241.5295, 1241.5265.

$HOSiPCOSi(CH_3)_2(CH_2)_3OH$ Compound XVII A solution of $CH_3SiPcOSi(CH_3)_2(CH_2)_3OCOCH_3$, $CH_3OH$, $K_2CO_3$ and $CH_2Cl_2$ was stirred, the reaction product was worked up, and the resulting $CH_3SiPcOSi(CH_3)_2(CH_2)_3OH$ was isolated. A solution of this compound and toluene was irradiated with light and the product was isolated and chromatographed: MS-HRFAB exact mass, m/z: calculated for $C_{37}H_{30}N_8O_3Si_2$ $(M)^+$, 690.1979; found, 690.1982, 690.1966.

$HOSiPcOSi(CH_3)_2(CH_2)_3NC_4H_8O$ Compound XIX A solution of $CH_3OSi(CH_3)_2(CH_2)_3Cl$, morpholine and $CH_3OH$ was refluxed and the resulting $CH_3OSi(CH_3)_2(CH_2)_3NC_4H_8O$ was isolated and distilled. A suspension of this compound, $CH_3SiPcOH$ and pyridine was partially distilled, and the $CH_3SiPcOSi(CH_3)_2(CH_2)_3NC_4H_8O$ was isolated and recrystallized. Finally, a mixture of this intermediate, toluene, $(C_2H_5)_3N$ and $H_2O$ was irradiated with light, and the product was isolated and recrystallized: MS-HRFAB exact mass, m/z: calculated for $C_{41}H_{37}N_9O_3Si_2$ $(M+H)^+$, 760.2636; found, 760.2620, 760.2610.

$AlPcOSi(CH_3)_2(CH_2)_3N^+(CH_3)_2(CH_2)_{11}CH_3I^-$ Compound XXI A mixture of $CH_3(CH_2)_{11}I$ and $AlPcOSi(CH_3)_2(CH_2)_3N(CH_3)_2$ was warmed, and the product was isolated and recrystallized: MS-HRFAB exact mass, m/z: calculated for $C_{51}H_{59}AlIN_9OSi$ $(M)^+$, 995.3472; found, 995.3444, 995.3428

$HOSiPcOSi(CH_3)_2(CH_2)_8N(CH_3)_2$ Compound XXII A solution of $CH_2=CH(CH_2)_6Br$, $(CH_3)_2NNH_2$ and ether was stirred, the reaction mixture was worked up with HCl, $NaNO_3$ and NaOH, and the resulting $CH_2=CH(CH_2)_6N(CH_3)_2$ was isolated and distilled. A solution of this compound, $(CH_3)_2SiHCl$, $CHCl_3$, $H_2PtCl_6.xH_2O$ and isopropanol was warmed and the $CH_3OSi(CH_3)_2(CH_2)_8N(CH_3)_2.HCl$ formed was isolated. Next, a suspension of this intermediate, $CH_3SiPcOH$ and pyridine was partially distilled, and the $CH_3SiPcOSi(CH_3)_2(CH_2)_8N(CH_3)_2$ obtained was isolated and recrystallized. Finally, a solution of this compound and $CH_2Cl_2$ was irradiated with light and the product was isolated, chromatographed, and recrystallized: MS-HRFAB exact mass, m/z: calculated for $C_{44}H_{45}N_9O_2Si_2$ $(M+H)^+$, 778.3313; found, 788.3300, 788.3290.

$SiPC[OSi(CH_3)_2(CH_2)_3NC_4H_8O_2$ Compound XXIII A suspension of $CH_3OSi(CH_3)_2(CH_2)_3NC_4H_7O$, $SiPc(OH)_2$ and pyridine was partially distilled, and the product was isolated and recrystallized: MS-HRFAB exact mass, m/z: calculated for $C_{50}H_{56}N_{10}O_4Si_3$ (M)$^+$, 944.3794; found, 944.3750, 944.3780.

HOSiPCOSi(CH$_3$)$_2$(CH$_2$)$_3$NC$_4$H$_8$S Compound XXIV A solution of CH$_3$OSi(CH$_3$)$_2$(CH$_2$)$_3$Cl, thiomorpholine and CH$_3$OH was refluxed and the resulting CH$_3$OSi(CH$_3$)$_2$(CH$_2$)$_3$NC$_4$H$_8$S was isolated and distilled. A suspension of this compound, CH$_3$SiPcOH and pyridine was partially distilled and the CH$_3$SiPcOSi(CH$_3$)$_2$(CH$_2$)$_3$NC$_4$H$_8$S formed was isolated and recrystallized. Finally, a mixture of this intermediate, toluene, (C$_2$H$_5$)$_3$N and H$_2$O was irradiated with light, and the product was isolated, chromatographed and recrystallized: MS-HRFAB exact mass, m/z: calculated for $C_{41}H_{37}N_9O_2SSi_2$ (M)$^+$, 775.2330; found, 775.2308 775.2310.

HOSiPcOSi(CH$_3$)$_2$(CH$_2$)$_3$N(CH$_2$)$_3$CH$_3$)$_2$ Compound XXV A solution of CH$_3$OSi(CH$_3$)$_2$Cl, (CH$_3$(CH$_2$)$_3$)$_2$NH and CH$_3$OH was refluxed and the resulting CH$_3$OSi(CH$_3$)$_2$(CH$_2$)$_3$N((CH$_2$)$_3$CH$_3$)$_2$ was isolated. A suspension of this compound, CH$_3$SiPcOH and pyridine was partially distilled, and the product was isolated and chromatographed. Finally, a mixture of this intermediate, toluene, (C$_2$H$_5$)$_3$N and H$_2$O was irradiated with light, and the product was isolated and recrystallized: MS-HRFAB exact mass, m/z: calculated for $C_{45}H_{47}N_9O_2Si_2$ (M+H)$^+$, 802.3470; found, 802.3434, 802.3435

HOSiPcOSi(CH$_3$)$_2$(CH$_2$)$_3$NCS Compound XXVI A mixture of CH$_3$OSi(CH$_3$)$_2$(CH$_2$)$_3$Cl, KNCS and dimethylformamide was warmed and the resulting CH$_3$OSi(CH$_3$)$_2$(CH$_2$)$_3$NCS was isolated A mixture of the compound, CH$_3$SiPcOH and pyridine was partially distilled and the CH$_3$SiPcOSi(CH$_3$)$_2$(CH$_2$)$_3$NCS formed was isolated, recrystallized and chromatographed. Finally, a solution of this intermediate and toluene was irradiated with light and the product was isolated and recrystallized: MS-HRFAB exact mass, m/z: calculated for $C_{38}H_{29}N_9O_2SSi_2$ (M)$^+$, 731.1704; found, 731.1696, 731.1669.

SiPc[OSi(CH$_3$)$_2$(CH$_2$)$_3$NC$_4$H$_8$NCH$_3$]$_2$ Compound XXX A suspension of CH$_3$OSi(CH$_3$)$_2$(CH$_2$)$_3$NC$_4$H$_8$NCH$_3$, SiPc(OH)$_2$ and pyridine was partially distilled, and the product was isolated and recrystallized: MS-HRFAB exact mass, m/z: calculated for $C_{52}H_{62}N_{12}O_2Si_3$ (M+H)$^+$, 971.4505; found, 971.4460, 971.4489.

HOSiPCOSi(CH$_3$)$_2$(CH$_2$)$_3$NC$_4$H$_8$N(CH$_2$)$_3$CH$_3$ Compound XXXI A suspension of piperazine, CH$_3$(CH$_2$)$_3$Br, toluene and K$_2$CO$_3$ was refluxed, and the resulting HNC$_4$H$_8$N(CH$_2$)$_3$CH$_3$ was isolated and distilled. A solution of this compound, CH$_3$OSi(CH$_3$)$_2$(CH$_2$)$_3$Cl and CH$_3$OH was refluxed, and the CH$_3$OSi(CH$_3$)$_2$(CH$_2$)$_3$NC$_4$H$_8$N(CH$_2$)$_3$CH$_3$ formed was isolated. Next, a suspension of this intermediate, CH$_3$SiPcOH and pyridine was partially distilled, and the CH$_3$SiPcOSi(CH$_3$)$_2$(CH$_2$)$_3$NC$_4$H$_8$N(CH$_2$)$_3$CH$_3$ obtained was isolated and chromatographed. Finally, a mixture of this compound, toluene (C$_2$H$_5$)$_3$N and H$_2$O was irradiated with light, and the product was isolated and recrystallized: MS-HRFAB exact mass, m/z: calculated for $C_{45}H_{46}N_{10}O_2Si_2$ (M+H)$^+$, 815.3422; found, 815.3424, 815.3423.

SiPc[OSi(CH$_3$)$_2$(CH$_2$)$_3$NC$_4$H$_8$NH]$_2$ Compound XXXII A solution of CH$_3$OSi(CH$_3$)$_2$(CH$_2$)$_3$Cl, piperazine and CH$_3$OH was refluxed, and the resulting CH$_3$OSi(CH$_3$)$_2$(CH$_2$)$_3$NC$_4$H$_8$NH was distilled. A suspension of this compound, SiPc(OH)$_2$ and pyridine was partially distilled and the product was isolated and recrystallized. MS-HRFAB exact mass, m/z: calculated for $C_{50}H_{58}N_{12}O_2Si_3$ (M+H)$^+$, 943.4192; found, 943.4160, 943.4213.

In Vitro Evaluation

Culture of Chinese Hamster V79-379 cells

Chinese hamster V79-379 lung fibroblasts were grown in monolayer culture in McCoy's 5A medium (Gibco Laboratories, Grand Island, N.Y.) augmented with 10% calf serum and buffered with 20 mM HEPES (pH 7.4).

Uptake of Phthalocyanines

Total uptake was determined by scraping the phthalocyanine-treated monolayer, collecting the cells on a glass-fiber filter, and extracting the phthalocyanine in ethanol, as previously described by Ramakrishnan, et al., 1989. (Ramakrishnan, N., M. E. Clay, M. F. Horng, A. R. Antunez, & H. H. Evans, "DNA Lesions and DNA Degradation in Mouse Lymphoma L5178Y Cells After Photodynamic Treatment Sensitized by Chloroaluminum Phthalocyanine", *Photochem. Photobiol*, in press, 1989). The amount of drug was determined by absorption at 674 nm and expressed relative to the number of cells, as measured in a Coulter cell counter on an aliquot of the cell population. Controls included cells not treated with drug, medium alone, and drug-containing medium without cells. The results of the total uptake of the various compositions of the present invention in comparison to AlPcCl are set forth below in Table 1.

Drug Treatment and Light Exposure

The cells were treated with 1 μM AlPcCl (from Eastman Kodak, Rochester, N.Y.) or with phthalocyanine compositions I–VI (0.5–1.0 μM final concentration in the medium) for 18 hours by adding the appropriate volume of a 1.0 mM stock solution in dimethylformamide (DMF) to the culture medium. The growth medium was replaced with 4 ml Hank's balanced salt solution (HBSS), and the cells were irradiated. The light source was a 500 W tungsten-halogen lamp located approximately 29 inches below the surface of a glass exposure tray. The visible light administered to the cells was filtered to allow passage of only that portion of the visible spectrum above 600 nm (Lee Primary red filter No. 106, Vincent Lighting, Cleveland, Ohio). The fluence rate was approximately 0.074 kJ/m$^2$/s at the level of the cell monolayer.

Growth Delay

At the time of light exposure, there were approximately $1.5 \times 10^5$ cells per 25 cm$^2$ flask. Following irradiation, the HBSS was replaced by 10 ml of fresh complete growth medium, and the cultures were returned to the 37° C. incubator. At various times before and after irradiation, duplicate cultures were trypsinized and counted. Controls included untreated cells and cells treated with light alone or drug alone. In addition, in each experiment, the drug to be tested was compared to a standard treatment, i.e. 1 μM AlPcCl for 18 hours followed by 12 kJ/m$^2$ light. The results of the growth delay analysis for each of the compositions I–VI in comparison to AlPcCl are set forth in Table 1 below.

Clonogenic Cell Survival

Cells were irradiated at a density of approximately $2 \times 10^6$ per 25 cm$^2$ flask. Immediately after irradiation, the cell monolayer was treated with trypsin, and appropriate aliquots were plated in triplicate to give 100 to 200 colonies in each 10-cm Petri dish. Cell survival was determined by the ability of the cells to form colonies containing at least 50 cells. The response of cells treated with 1 μM AlPcCl and light was compared in each experiment.

TABLE 1

Activities of Several Al and Si Phthalocyanines

| Comp. | Structure | Conc. (μM) | Uptake | Growth Delay (12 kJ/m$^2$) | $F_{10}$(AlPcCl)/ $F_{10}$(Pc) | $CF_{10}$(AlPcCl)/ $CF_{10}$(Pc) |
|---|---|---|---|---|---|---|
|  | AlPcCl | 1.0 | 1.0 | 1.0 | 1.0 | 1.0 |
| I | AlPcOSi(CH$_3$)$_2$)CH$_2$)$_3$N(CH$_3$)$_2$ | 1.0 | 2.3 | 2.1 | 0.94 | 0.51 |
| II | AlPcOSi(CH$_3$)$_2$(CH$_2$)$_3$N(CH$_3$)$_3$ $^+$I$^-$ | 1.0 | 1.8 | 3.4 | 0.99 | 0.72 |
| III | CH$_3$SiPcOSi(CH$_3$)$_2$(CH$_2$)$_3$N(CH$_3$)$_2$ | 1.0 | 0.07 | 0.05 | ND | ND |
| IV | HOSiPcOsi(CH$_3$)$_2$)(CH$_2$)$_3$N(CH$_3$)$_2$ | 0.5 | 1.3 | >3 | 1.85 | 3.9 |
|  |  | 1.0 | 1.64 | ND | 4.25 | 3.5 |
| V | HOSiPcOSi(CH$_3$)$_2$(CH$_2$)$_3$—N(CH$_3$)$_3$$^+$I$^-$ | 1.0 | 0.3 | 0 | 0.59 | 3.0 |
| VI | SiPc(OSi(CH$_3$)$_2$(CH$_2$)$_3$—N(CH$_3$)$_3$)$^+$I$^-$)$_2$ | 1.0 | 0.1 | 0.05 | ND | ND |

Results of Testing Compounds I–VI in V79-379 cell culture

All of the compounds have been examined for the extent of cellular uptake after exposure of V79 cells to 1 μM or less in complete medium, and the data of Table 1 are presented relative to the uptake from 1 μM AlPcCl, which was 0.723±0.172 nmole/10$^7$ cells (mean ±S. D., 25 determinations). Compounds I, II, and IV were taken up into the cells more efficiently than was AlPcCl under these conditions. In particular, when the concentration of Compound IV was 1 μM in the medium, the uptake into the cells was sufficiently high that some of the uptake and phototoxicity studies were repeated at 0.5 μM. Compounds III, V, and VI were less effectively incorporated into V79 cells.

Photodynamic action against V79 cells was assessed both by measurement of growth delay and by assay of the loss of clonogenicity. With both assays, none of the compounds showed any dark toxicity at concentrations of 1.0 μM or less for up to 18 hours.

The inhibition of V79 culture growth was measured during a three day period following red light irradiation (12 kJ/m$^2$) of phthalocyanine-pretreated cells. With each of the active compounds, as well as with AlPcCl, there was an initial decrease in cell density, as dead cells became detached from the monolayer. Thereafter, the cell number per flask increased, as living cells grew and divided. The time for the cell density to recover to the level at the time of light exposure was considered the growth delay. Cells treated with 1 μM AlPcCl for 18 hours and 12 kJ/m$^2$ light were used for comparison purposes in each experiment and demonstrated a growth delay of approximately 24 hours. The ratio of the growth delay for the test photosensitizer and the growth delay for AlPcCl measured in the same experiment is recorded in Table 1. There was less inhibition of culture growth when cells were exposed to compounds III, V, or VI as expected from the poor cellular uptake of these drugs. In contrast, substantial inhibition was observed for compounds I, II, and IV. A value of >3 for compound IV (Table 1) indicates that the cell density had not recovered to the initial level during the three day observation period.

Photocytotoxicity of the phthalocyanines compounds I to VI was also assessed by clonogenic assay (Table 1, FIG. 1). In all experiments, 1 μM AlPcCl was included for comparison purposes. From the survival curves (FIG. 1), the fluence reducing the cell survival to 10% ($F_{10}$) was obtained. The ratio of the $F_{10}$ for AlPcCl and the $F_{10}$ for the test compound is recorded in Table 1. Compounds I and II appear to be nearly as efficient photosensitizers as AlPcCl, while compound IV (assayed at half the concentration) was almost twice as efficient as the standard AlPcCl. Clonogenic assays were not conducted for compounds III and VI, since the data on uptake and growth delay suggested that these compounds would have poor activity. However, in spite of the low efficiency of compound V in inhibiting cell growth, survival measurements were made for this compound, because it was taken up into V79 cells somewhat more efficiently than compounds III and VI.

Figure 2:
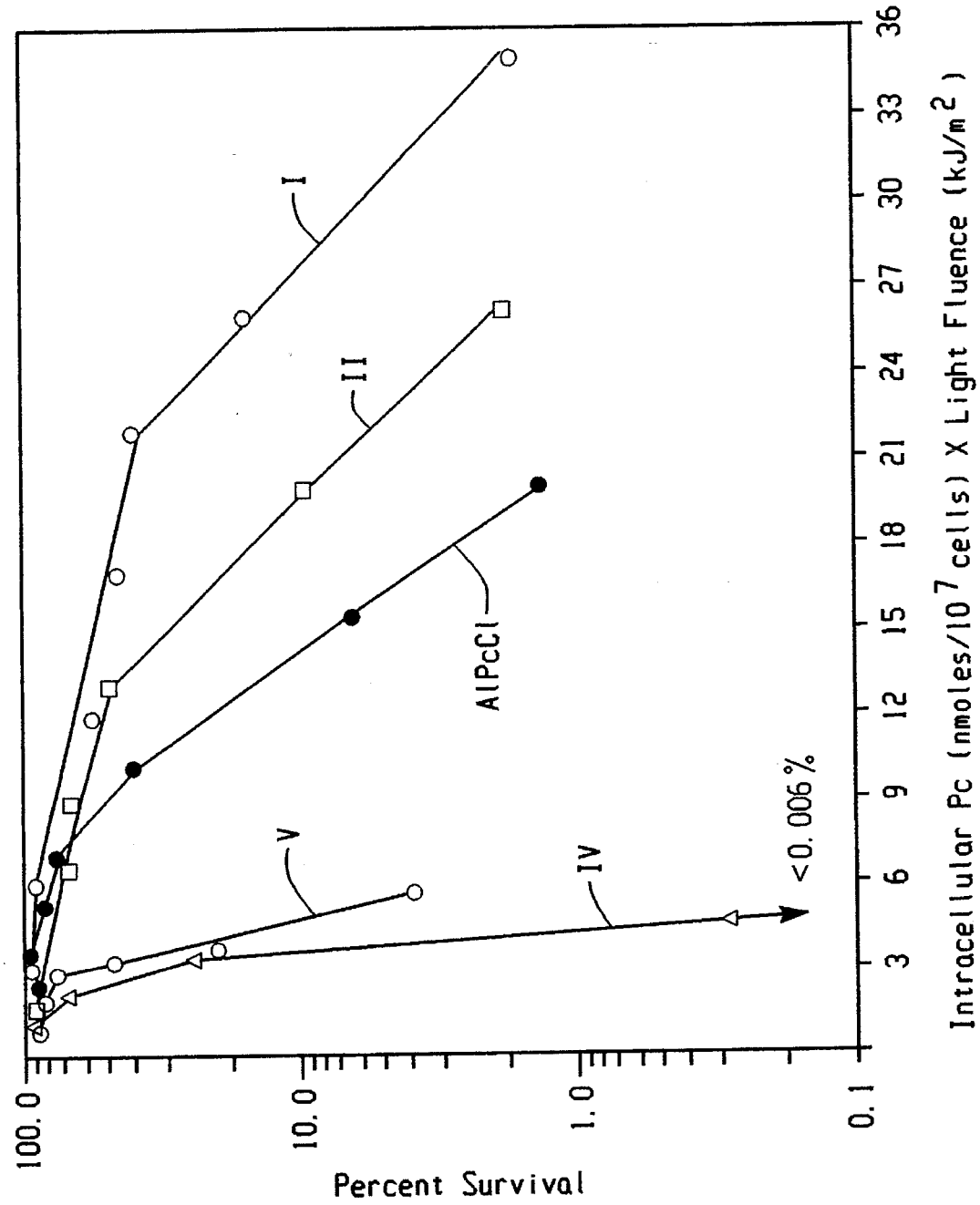
FIG. 2 is a graph demonstrating the percent survival of the compositions of the present invention in comparison to ALPcCl in relation to intracellular phthalocyanine (nmole/ $10^7$ cells) and light fluence (kJ/m²). In this regard, in FIG. 2 the data of FIG. 1 were replotted as a function of the product of the amount of cell-associated phthalocyanine and the light fluence.

In order to take differences in cellular uptake into consideration in the assessment of the relative efficiency of these phthalocyanines as photosensitizers of V79 cells, the survival data were replotted against the product of intracellular phthalocyanine concentration and light fluence (FIG. 2). From these curves, the product of intracellular concentration and light fluence reducing survival to 10% ($CF_{10}$) was obtained, and comparisons of the values for AlPcCl and the test compounds are recorded in Table 1. By this and the other criteria, compound IV appears to be the most efficient photosensitizer. However, when consideration is given to the lesser cell uptake of compound V, it appears to be about as strong a photosensitizer as compound IV.

Discussion of Testing Compounds I–VI in V79 Cell Culture Photocytotoxicity

The low activity of compounds III and VI appears to be due to poor cell uptake. Both of these compounds have functional groups on both faces of the phthalocyanine ring, and it is possible that one face of the ring must be free for proper interaction with target biomolecules. Either Si phthalocyanine with no more than a hydroxyl group on one face (IV) or Al phthalocyanine with one face free of substituents (I and II) allows efficient cellular uptake as well as a high degree of cellular inactivation. Thus, both tertiary and quaternary amines appear to be efficacious structures. Compound V is an anomaly. Although it has features on either face of the phthalocyanine ring found on active molecules, the combination appears not to allow efficient cellular uptake. However, that which is incorporated into the cells has good photodynamic activity.

The results of the in vitro biological tests of the new phthalocyanines compounds I to VI are an important introduction to the design of a new class of photosensitizers. The results suggest that tertiary and quaternary amines may be an important class of structures to be explored. The axial ligands of the series of compounds listed in Table 1 are simpler than the corresponding ligand of the original diethylamine which served as a prototype. The simpler ligands appear to have the advantages of stability in solution, making them easier to study. The instability of the diethylamine precluded precise measurements of the concentration of the active species at the time of irradiation. Therefore, the true photosensitizing activity of the prototype compound may also be high.

Evaluation of Phthalocyanine Compounds VII–XV, XVII–XIX, XXI–XXVIII, and XXX–XXXII Uptake of Phthalocyanine Compounds VII–XV, XVII–XIX, XXI–XXVIII, and XXX–XXXII into V79 Cells In addition to the phthalocyanine compounds I to VI, several other new phthalocyanine compounds have proven to be effective in treating cancer. V79 cells Chinese hamster lung fibroblasts were cultured using the cell culture methods described above. The phthalocyanines listed in table 2 were added to the cultures typically at concentrations of 1 μM, 2 μM, and/or 4 μM and incubated for 18 hours, after which aliquots of the cells were counted and other aliquots were collected on a glass fiber filter. When the filters were dry, the phthalocyanines were extracted into ethanol and the absorption determined at the peak wavelength, usually 668 nm. Values were converted to nmoles taken up by $10^6$ cells, using an extinction coefficient of $2.93 \times 10^5$. The cellular uptake of the phthalocyanines are presented in Table 2.

TABLE 2

Uptake of Additional Phthalocyanines Into V79 Cells

| Pc Num. | n Moles/$10^6$ cells | | | n Moles/$10^6$ cells/μM |
|---|---|---|---|---|
| | 1 μM | 2 μM | 4 μM | |
| IV | 0.7 ± 0.2 | 3.1 ± 0.3 | 4.6 ± 2.9 | 1.1 |
| VII | 0.2 ± 0.03 | | 1.1 ± 0.5 | 0.2 |
| VIII | 0.1 ± 0.04 | | 0.8 ± 0.01 | 0.2 |
| IX | 0.1 ± 0.1 | | 1.8 ± 0.8 | 0.3 |
| X | 0.6 ± 0.2 | | 3.3 ± 1.4 | 0.7 |
| XI | 0.1 | | 0.3 ± 0.1 | 0.1 |
| XII | 2.1 ± 1.2 | | 4.6 ± 1.5 | 1.6 |
| XIII | | | 1.7 ± 0.3 | 0.4 |
| XIV | 0.03 ± 0.01 | | 0.05 ± 0.01 | <0.05 |
| XV | 0.01 ± 0.01 | | 0.14 ± 0.12 | <0.05 |
| XVI | 0.2 ± 0.2 | | 0.7 ± 0.20 | 0.2 |
| XVII | | | 1.7 ± 0.2 | 0.4 |
| XVIII | 0.3 ± 0.1 | | 3.6 ± 0.6 | 0.3* |
| XIX | 0.3 ± 0.1 | | 2.4 ± 0.5 | 0.3* |
| XXI | 1.2 ± 0.2 | | 5.8 ± 0.4 | 1.3 |
| XXII | | | | ND |
| XXIII | | | | ND |
| XXIV | 0.003 ± 0.001 | | 1.3 ± 0.1 | <0.05* |
| XXV | 0.02 ± 0.02 | | 1.5 ± 0.3 | <0.05* |
| XXVI | | | | ND |
| XXVII | 1.8 | | 5.0 ± 0.01 | 1.5 |
| XXVIII | 1.2 ± 0.2 | 3.6 ± 1.0 | 11.4 ± 0.05 | 1.2* |
| XXX | | | | ND |
| XXXI | | 0.61 ± 0.1 | | 0.3 |

In the last column, wherever possible, a composite value was calculated, in order to have a single number for the purposes of ranking the uptake efficiency of the compounds. For most compounds, the average of all the data has been calculated and rounded to the first decimal. Where all values are <0.05, the data are presented as <0.05. An asterisk (*) indicates that an average uptake value, which is the average of the phthalocyanine doses would be higher than the listed value which is for 1 μM.

It appears from Table 2 that the uptake of PcXVIII, PcXIX, PcXXIV, PCXXV, and PcXXVIII are not linearly dependent upon the phthalocyanine concentration in the medium. PcIV, PcXII, PcXXI, PcXXVII and PcXXVIII are taken up particulary well by the V79 cells.

Clonogenicity studies using Phthalocyanine Compounds VII–XV, XVII–XIX, XXI–XXVIII, and XXX–XXXII into V79 Cells Using the cell culture methods described above, V79 cells Chinese hamster lung fibroblasts were treated with either 0.5 or 1.0 μM of the phthalocyanines listed in Table 3. About 18 hours thereafter, the cells were irradiated with increasing doses of 675 nm broad band red light from a 500 W tungsten-halogen lamp fitted with a 600 nm high pass filter, to determine the light dosage that would kill 90% of the phthalocyanine treated cells. Where 90% of the cells were not killed, the maximum percent of cells killed were determined, (expressed as % survival) and the related light dosage recorded. The results are presented in Table 3.

TABLE 3

EVALUATION OF PHTHALOCYANINE COMPOUNDS IN KILLING V79 CELLS USING PHOTODYNAMIC THERAPY

| Pc | Concn. (μM) | LD 90 (kJ/m$^2$) | Maximum Effect (% survival at kJ/m$^2$) | n Moles/$10^6$ cells/μM (from Table 2) |
|---|---|---|---|---|
| IV | 0.5 | 4 | | 1.1 |
| VII# | 0.5 | 4 | | 0.2 |
| VIII | 1 | | 94% at 30 | 0.2 |
| IX | 0.5 | | 44% at 9 | 0.3 |
| X | 0.5 | 7 | | 0.7 |
| XI | 1 | | 100% at 20 | 0.1 |
| XII | 0.5 | 3.3 | | 1.6 |
| XIII | 1 | | 88% at 15 | 0.4 |
| XIV | 1 | | 93% at 10 | <0.05 |
| XV | 4 | | 81% at 20 | 0.05 |
| XVI | 4 | | 100% at 10 | 0.2 |
| XVII | 1 | | 19% at 10 | 0.4 |
| XVIII | 1 | 7 | | 0.3* |
| XIX | 1 | | 81% at 10 | 1.3 |
| XXI | 0.5 | 15* | | ND |
| XXII | 0.5 | 10 | | ND |
| XXIV | 0.5 | | 100% at 10 | <0.05 |
| XXV | 0.5 | | 87% at 8 | <0.05 |
| XXVI | 1 | | 100% at 30 | ND |
| XXVII | 0.5 | 6.8 | | 1.5 |
| XXVIII | 0.5 | 1.8 | | 1.2* |
| XXX* | | | 30% at 10 | ND |
| XXXI | 0.5 | | 30% at 10 | 0.3 |

*not totally soluble at 0.5 mM
Preplated data only

As shown in Table 3, PcIV, PcVII, PcXII, and PcXXVIII achieved the LD 90 at the lowest light dosage, and thus are the most active photosensitizers, that is they are the most active at killing V79 cells.

For comparison, the phthalocyanine uptake values presented in Table 2 were also presented in the last column of Table 3. As shown in Table 3, some, but not all, of the differences in photosensitizing activity among phthalocyanines can be explained by differences in uptake. For example, PcXXVIII which has the highest activity in killing V79 cells of all of the phthalocyanines also has a high uptake. The uptake of Pc XXVIII at 1 μM is less than that for PcXII, whereas its photodynamic killing efficiency is superior to PcXII when analyzed at 0.5 μM.

It is not surprising that often phthalocyanines with poor uptake are relatively less active in photodynamic therapy, whereas the most active phthalocyanines demonstrate a relatively high uptake. However, uptake and activity are not always correlated. For example, PcVII has poor uptake but one of the better photosensitizers. PcXIX has poor uptake but is less active as a photosensitizer, whereas PcXVIII, with similar uptake, demonstrated good activity. Many factors contribute to determination of the photosensitizer efficiency, including physical state in the cells and localization.

Assessment of Photodynamic Efficiency of Additional Phthalocyanines in L5178Y-R Cells Mouse lymphoma L5178y-R (hereinafter also referred to as "LY-R") cells were grown in suspension culture as described in Ramakrishnan N., Oleinick, N. L. Clay, M. E., Horng, M. F., Antunez, A. R., and Evans H. H., DNA lesions and DNA degradation in mouse lymphoma L5178Y cells after photodynamic treatment sensitized by chloroaluminum phthalocyanine. Photochem. Photobiol. 50, 373–378, 1989 and Agarwal, M. L., Clay, M. E., Harvey, E. J., Evans, H. H., Antunez, A. R., and Oleinick, N. L. Photodynamic therapy induces rapid cell death by apoptosis in L5178Y mouse lymphoma cells. Cancer Res., 51, 5993–5996, 1991.

The cells were used while in exponential growth. Stock solutions of either 0.5 or 1 mM of PcIV, PcXII, PcX, PcXVIII were prepared in dimethylformamide unless otherwise indicated and added to the 10 mL medium at a rate of 1 µL per mL. After allowing 18 hours for uptake of the phthalocyanine into the cells, the flasks containing the cultures were placed on a glass exposure tray above a 500-W tungsten-halogen lamp. The exposure tray was fitted with a 600-nm high-pass filter. Flasks were exposed to various fluences of red light (up to 30 kJ/m$^2$) at a fluence rate of approximately 74 W/m$^2$). After irradiation, the cells were collected by centrifugation.

For measurement of clonogenic cell survival, aliquots were plated in medium containing soft agar as described in Ramakrishnan N., Oleinick, N. L. Clay, M. E., Horng, M. F., Antunez, A. R., and Evans H. H., DNA lesions and DNA degradation in mouse lymphoma L5178Y cells after photodynamic treatment sensitized by chloroaluminum phthalocyanine. Photochem. Photobiol. 50, 373–378, 1989. The aliquots were plated in sufficient numbers to produce 50–200 colonies. The dishes were kept in an incubator at 37° C. in an atmosphere of 5% $CO_2$ and 95% air for 10–14 days to allow viable cells to form colonies. Colonies were counted by eye. Controls treated with the phthalocyanine alone had plating efficiencies of ~90%. The plating efficiencies of the treated cells are normalized to the plating efficiencies of control cells in each experiment. For measurement of the induction of apoptosis, DNA was isolated from the treated and control cells 2 hours after photodynamic therapy, subjected to electrophoresis on 1.5% agarose, stained with ethidium bromide, and visualized by UV transillumination, as described in Agarwal et. al. The results are shown in Tables 4, 5 and 6 and in FIG. 3.

In Table 4 each phthalocyanine was present at 0.5 µM, and the normalized plating efficiencies are presented as mean and standard deviation at each fluence tested. The results show that all four phthalocyanines are active photosensitizers for photodynamic therapy. Based on their relative ability upon irradiation with various fluences of red light to reduce tumor cell survival, these phthalocyanines are ranked from the most active photosensitizers to the least active: PcIV, PcXII, PcX, PcXVIII. This relative activity of these four phthalocyanines is the same as obtained from screening in V79 cells.

Figure 3:
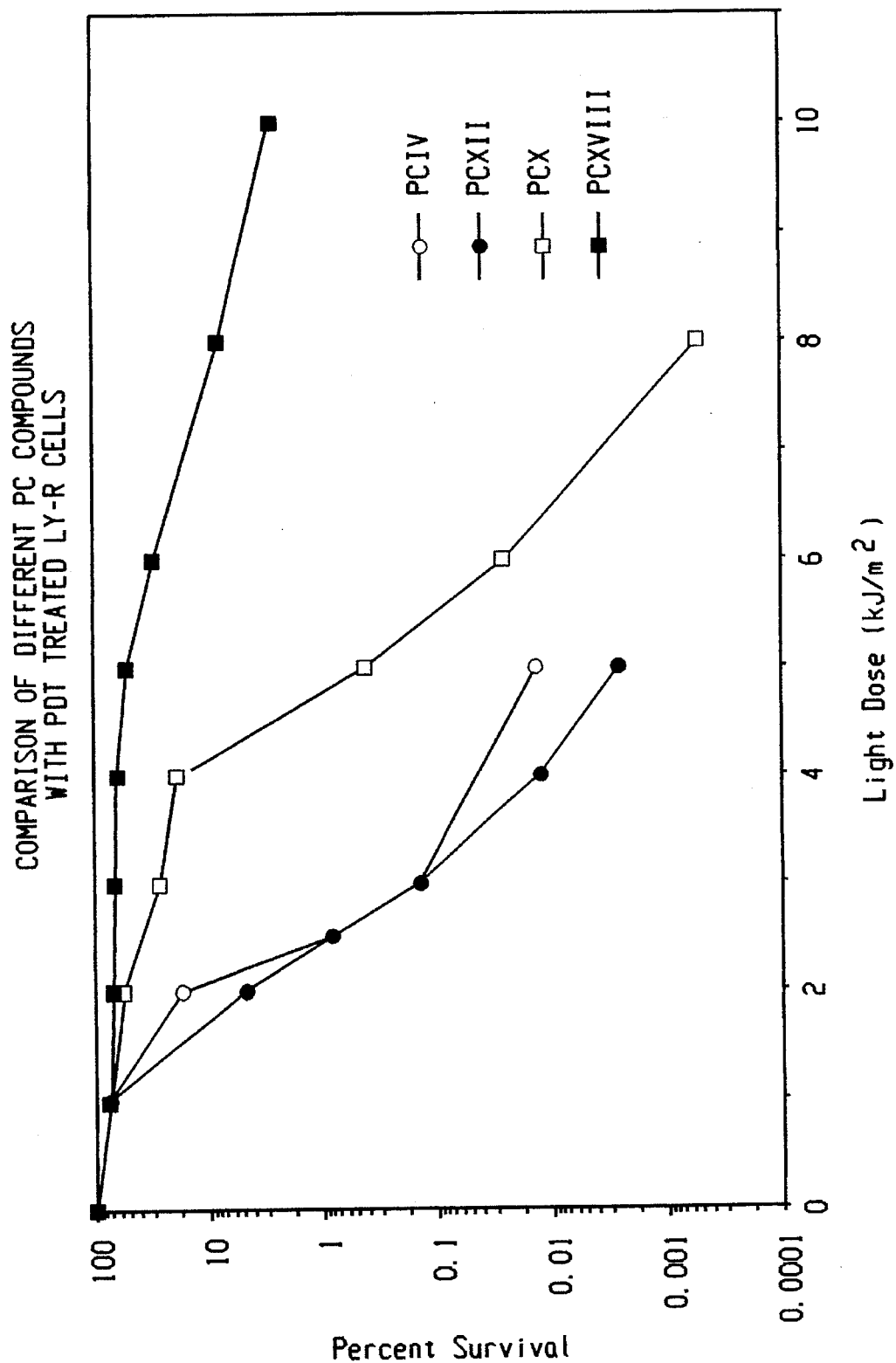
FIG. 3 is a graph which compares the percent survival of L5178Y strain R cells receiving photodynamic therapy and treated with: PcIV, represented by the open circles; PcXII, represented by the solid circles; PcX, represented by the open squares; and PcXVIII, represented by the solid squares, at varying doses of light.

FIG. 3 shows the average plating efficiencies from Table 4 plotted against the fluence for each Pc.

TABLE 5

| Clonogenic Assay of Phthalocyanines | | | |
|---|---|---|---|
| Pc | Concentration (µM) | LD$_{50}$ (kJ/m$^2$) | LD$_{90}$ (kJ/m$^2$) |
| Pc IV | 0.5 µM | 1.38 | 2.15 |
| Pc X | 0.5 µM | 2.38 | 4.19 |
| Pc XII | 0.5 µM | 1.11 | 1.70 |
| Pc XVIII | 0.5 µM | 5.00 | 7.81 |

Table 5 shows the fluence that reduces the cell survival to 50% and to 10% and which are given as LD$_{50}$ and LD$_{90}$, respectively. The most active compound of the phthalocyanines shown in Table 5 is PcXII. PcXII when present in the culture medium at 0.5 µM requires less light, that is the lowest fluence, to kill either 50% or of the cells. PcIV is about 80% as active as PcXII, PcX is 44% as active as PcXII and PcXVIII is 22% as active as PcXII.

TABLE 6

| Relative Capacity of Phthalocyanines to Induce Apoptosis | | | |
|---|---|---|---|
| | Minimum Demonstrated Condition | | |
| Pc | Concentration (µM) | Fluence (kJ/m$^2$) | C × F (µm × kJ/m$^2$) |
| Pc IV | 0.4 | 3.0 | 1.2 |
| Pc VII | 0.5 | 3.0 | 1.5 |
| Pc IX | 0.3 | 12.0 | 3.6 |
| | 0.5 | 8.0 | 4.0 |
| | 1.0 | 12.0 | 12.0 |
| Pc X | 0.5 | 6.0 | 3.0 |
| | 1.0 | 3.0 | 3.0 |
| Pc XII | 0.4 | 3.0 | 1.2 |

TABLE 4

| Comparison of Different Phthalocyanine Compounds In PDT-treated LY-R cells | | | | | | | | |
|---|---|---|---|---|---|---|---|---|
| LIGHT DOSE | Pc IV | | Pc XII | | Pc X | | Pc XVIII | |
| (kJ/m$^2$) | AVG. | SD | AVG. | SD | AVG. | SD | AVG. | SD |
| 0 | 100 | | 100 | | 100 | | 100 | |
| 1 | 80.9 | 11.4 | 82.2 | 8.6 | | | | |
| 2 | 19.7 | 2.9 | 5.23 | 0.86 | 71.8 | 15.4 | 81.8 | 6.0 |
| 2.5 | 0.82 | 0.09 | 0.90 | 0.15 | | | | |
| 3 | 0.16 | 0.10 | 0.15 | 0.01 | 30.1 | 3.7 | 73.6 | 4.8 |
| 4 | | | 0.014 | 0.002 | 20.5 | 1.1 | 64.0 | 7.0 |
| 5 | 0.014 | 0.001 | 0.0027 | 0.0008 | 0.43 | 0.19 | 52.1 | 6.2 |
| 6 | | | | | 0.031 | 0.014 | 33.8 | 5.8 |
| 8 | | | | | 0.00058 | 0.0003 | 9.13 | 1.52 |
| 10 | | | | | | | 3.0 | 3.0 |

TABLE 6-continued

Relative Capacity of Phthalocyanines to Induce Apoptosis

| | Minimum Demonstrated Condition | | |
|---|---|---|---|
| Pc | Concentration ($\mu$M) | Fluence (kJ/m$^2$) | C × F ($\mu$m × kJ/m$^2$) |
| Pc XVIII | 0.5 | 10.0 | 5.0 |
| | 1.0 | 3.0 | 3.0 |
| Pc XXI | 0.5 | 15.0 | 7.5 |
| Pc XXII | 0.5 | 10.0 | 5.0 |
| Pc XXVIII | 0.3 | 3.0 | 0.9 |
| Pc XXX (DMF-Tween 80) | 0.5 | 15.0 | 7.5 |
| Pc XXXII (DMF-Tween 80) | 0.5 | 5 | 2.5 |

Table 6 shows that photodynamic therapy with the phthalocyanine compounds listed causes L5178Y cells to undergo apoptosis as the mode of cell death. Cells were treated with various concentrations of the compounds listed in the table and various light fluences. DNA gels were prepared and examined for the characteristic "ladder" pattern of DNA fragments. For each Pc, the minimum total PDT dose tested (calculated as the product of the minimum phthalocyanine concentration and the minimum fluence) which produced visible DNA fragments is recorded. PcXXX and PcXXXII were not soluble in DMF and were suspended and partially solubilized in DMF/Tween 80 for this assay. PcIX is unusual in that its activity increases and then decreases as the concentration is raised. PcX was added at concentrations of 0.5 and 1.0 $\mu$M; the same minimum value for the C×F product was obtained in both cases. PcXVIII was also added at 0.5 and 1.0 $\mu$M. The minimum value of C×F differed only slightly for the two conditions. PcV, PcVI, PcVIII, PcXI, PcXIV and PcXV, when evaluated at a concentration of 1 $\mu$M at a fluence of 30 kJ/m$^2$ did not induce apoptosis. Compound PcXVI at a concentration of 4 $\mu$M and a fluence of 20kJ/m$^2$ for 2 hours did not induce apoptosis.

In vivo Evaluation of Phthalocyanine Compounds VII–XV, XVII–XIX, XXI–XXVII, and XXX–XXXII The relative effectiveness at reducing tumor volume of selected phthalocyanine compounds at a given dosage was compared in vivo. RIF-1, i.e., radiation-induced fibrosarcoma, tumors were implanted into the backs of C3H/HeN mice. One tumor was implanted per mouse. Each of the phthalocyanine compounds listed in Table 7 was sonicated and vortexed in corn oil to produce a suspension. When the tumors reached 5–7 cm in diameter and 2–3 mm in thickness, each mouse received 1 mg/kg in 0.1 ml of the corn oil, of the phthalocyanine suspension. For comparison, select mice received a conventional photosensitizer; either 5 mg/kg of chloroaluminum phthalocyanine tetrasulfonate, herein also referred to as "AlPcTS" in phosphate buffered saline or 5 mg/kg of Photofrin®-II in 5% dextrose. Twenty-four hours after the photosensitizers were administered, the tumors were irradiated with visible radiation delivered by an argon-pumped dye laser. The mice that received a phthalocyanine photosensitizer received light having a wavelength of 675 nm and the mice that received the Photofrin® II photosensitizer received light having a wavelength of 630 nm. Each tumor received 135 J/cm$^2$ of radiation. Tumor size was measured every day using calipers. The initial tumor volume was 50±10 mm$^3$. Tumor volume was calculated according to the hemiellipsoid model by the formula:

$$V = \frac{1}{2} \cdot \frac{(4\pi)}{3} \times \left( \frac{1}{2} \times \frac{w}{2} \right) \times h$$

Where l is length
Where W is width
Where H is height
The tumor response is shown in Table 7.

TABLE 7

Comparative Responses of RIF-1 Implanted Tumors to PDT With Select Phthalocyanine Compounds

| Photosensitizer | Tumor Responses at 24 hours | Doubling Time of Initial Tumor Volume after PDT in days |
|---|---|---|
| Pc XXVIII | complete | 24 |
| Pc XII | complete | 20 |
| Pc IV | near complete | 16 |
| Pc XVIII | near complete | 12 |
| Pc IX | near complete | 11 |
| Pc V | moderate | 6 |
| Pc VIII | slight | 4 |
| AlPcTS* | substantial | 7 |
| Photofrin ™-II* | near complete | 12 |
| controls | | 4 | complete- no evidence of any tumor mass in any animal; only the scar from the photodynamic therapy was evident.
near complete-no evidence of any tumor mass in four or five animals; only some tumor mass in one or two animals.
substantial- a significant tumor shrinkage occurred in all animals. In some animals the tumor response was complete, yet in others the response was not complete.
moderate- some tumor shrinkage was evident in some animals. In animals with some tumor shrinkage, scar formation was evident.
slight-some tumor decrease occurred in one or two mice.

While the tumor volume in the control mice doubled in four days, the doubling of tumor volume was delayed in the animals treated with each of the compounds except PcVIII. PcXXVIII, PcXII, PcIV, PcXVIII, PcIX were particularly effective in reducing tumor volume.

Histological examination of tumors treated with PcIV revealed the presence of apoptotic bodies in the tumor. Analysis of tumors treated with Pc IV showed DNA fragments whose sizes were multiples of 180–200 base pairs.

As can be seen from Table 7, Pc XXVIII, Pc XII and Pc IV significantly impair the growth of the tumors and are the most preferred photosensitizers for the treatment of cancer, because of effectiveness at set dosage of phthalocyanine.

Not only do the phthalocyanine compounds of the present invention reduce tumor volume, they are capable of eliminating tumors completely particularly upon multiple exposures to radiation.

Complete inhibition of tumors by PDT with PcIV

As occurs with PF-II-PDT, regrowth of tumors from the tumor margins occurred in the animals treated Pc IV, followed by the exposure to light. This regrowth possibly originates from the cells which somehow escape irradiation.

To overcome the regrowth, RIF-1 tumors were implanted in C3H/HeN mice, and the mice were treated with PcIV followed by multiple exposures to light. For multiple exposures to light to be successful, the tumor tissue must retain sufficient levels of the photosensitizer over the exposure period.

Since pharmacokinetic data indicated that Pc IV is retained in tumor tissue even after 7 days of its administration, Pc IV was administered once at the dose of 1 mg/kg body weight in corn oil or entrapped in DPPC liposomes.

Thereafter, the tumors were irradiated with an argon ion pumped dye laser tuned at 675 nm for the total light dose of 135 J/cm$^2$ (75 mW/cm$^2$). The tumors were irradiated with multiple exposures of 675 nm laser light, at varying times, as shown in Table 8.

TABLE 8

Responses of RIF-1 implanted tumors tO PcIV followed by multiple exposures to light

| day of exposure | % of Mice Surviving | | |
|---|---|---|---|
| | corn oil 15 days | liposomes 30 days | liposomes 120 days |
| 2 | 100 | 100 | N/A |
| 2 and 3 | 100 | 100 | N/A |
| 2, 3, and 4 | 100 | 0 | 0 |
| 2, 3, 4, 5 and 6 | 100 | 0 | 0 |
| 2–6 | 100 | 0 | 0 |
| 2 and 7 | 100 | 100 | N/A |

Where Pc IV was given in corn oil, regrowth of tumors was evident 15 days after photodynamic therapy in all the multiple exposure protocols. However, when the PcIV was administered entrapped in DPPC liposomes, complete tumor cure was evident in those mice which were irradiated three, four or five times at an interval of 24 hours. No tumor regrowth occurred even at 120 days after the photodynamic therapy. Indeed, at the time the mice were sacrificed 300 days after the light treatment, there was no evidence of tumor regrowth. Tumor regrowth occurred 30 days after photodynamic therapy only in those animals which were irradiated only one or two times either at 24 or 120 hour intervals. One reason for this differential effect may be related to the pharmacokinetics of the dye, that is the dye may have been retained in the tissue for a long period which permitted multiple exposures to be effective. Alternatively, the administration of Pc IV, via DPPC liposomes may enhance uptake and retention of PcIV by the tumor cells.

Squamous Cell Carcinoma

A single cell suspension of human squamous cell carcinoma was injected subcutaneously into the back of Harlen-Sprague Dawley athymic nude mice. Thereafter on day 15 the mice were injected with 5 mg/kg of Pc IV suspended in 0.1 ml corn oil For comparison 5 mg/kg body weight of Photofrin® was administered. The results are shown below in Table 9.

TABLE 9

Tumor Response and Cure following Photodynamic Therapy

| No of Test Animals | Pc IV Concentration (mg/kg) | 675 nm Light Dose Density (J/cm$^2$) | 675 nm Power Density (nW/cm$^2$) | Illumination Time (min) | % Tumor Response[a] | % Tumor Cure[b] |
|---|---|---|---|---|---|---|
| 5 | 0.0 | 75 | 75 | 15 | 0 | 0 |
| 5 | 1.0 | 0 | 0 | 0 | 0 | 0 |
| 5 | 1.0 | 35 | 75 | 15 | 40 | 0 |
| 5 | 1.0 | 75 | 75 | 15 | 80 | 60 |
| 5 | 1.0 | 135 | 75 | 15 | 100 | 100 |

[a]Tumor flat, necrotic, measured 24 hours post illumination.
[b]No tumor at 7 days post treatment.

As can be seen from Table 9, 1 mg/Kg Pc IV followed by 135 J/cm$^2$ of 675 nm light at a power Density of 75 mW/cm$^2$ for 15 minutes eliminated the tumors in 100% of the mice.

Treatment of chemically induced skin tumors.

6-week-old female SENCAR mice received a single topical application of 5 μg DMBA in 0.2 ml acetone on the dorsal skin as tumor initiator. One week later, the animals were started on twice-weekly topical applications of 1 μg TPA in 0.2 ml acetone as tumor promoter. All of the animals developed tumors at 12 weeks. Mice that developed 4–5 tumors per animal averaging 5–8 mm in diameter and 2–5 mm in thickness were used. Pc IV, entrapped in DPPC liposomes was administered intraperitoneally at doses of either 0.5 or 1.0 mg/kg and 24 hrs later the tumor area was illuminated with light from an argon pumped dye laser tuned at 675 nm for a total light dose of 135 J/cm$^2$ (75 mW/cm$^2$). All possible controls were included; either the animals were untreated, treated only with laser light or treated only with Pc IV alone.

Figure 4:
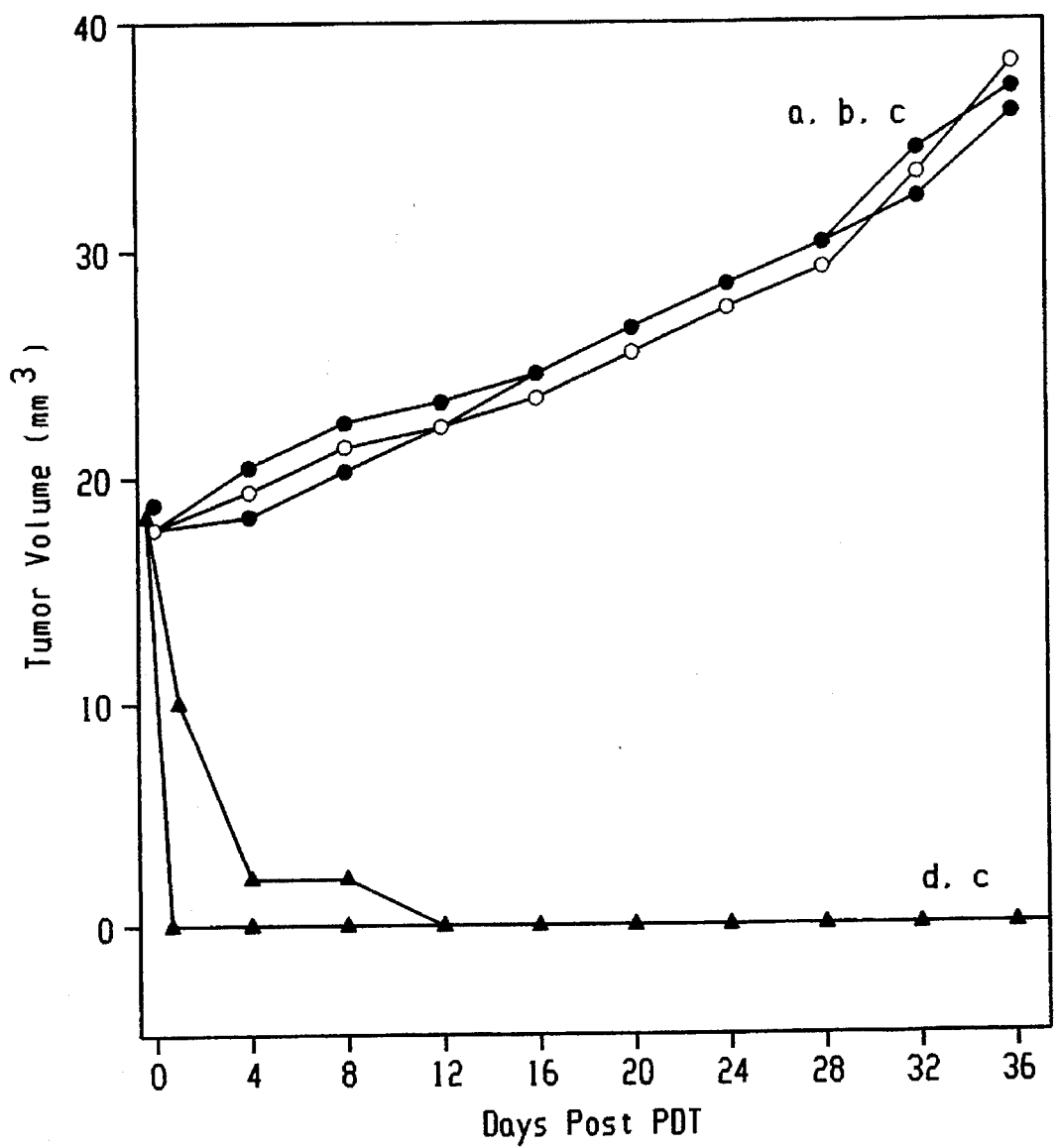
FIG. 4 shows the tumor volume response of chemically-induced benign skin papillomas in SENCAR mice, to photodynamic therapy with PcIV.

Curves for animals after PDT with Pc IV at the doses of 0.5 and 1.0 mg/kg are shown by d and e in Figure 4. As shown in FIG. 4 the mice treated with PcIV and light showed a decrease in tumor volume which eventually decreased to 0 volume, that is, no tumor was measurable. The tumor did not return for the length of the study, 34 days. In contrast, the control tumor volume consistently increased over time.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

In addition, although the present invention has been described with reference to the effectiveness of the phthalocyanine compositions in photodynamic therapy for the destruction of cancer tissue, it is well understood by those skilled in the art that the compositions of the invention may be well suited for other therapeutic purposes. Along this line, it is contemplated that other possible uses of the composition of the present invention include:

(1) the purging of bone marrow for autologous bone marrow transplantation;

(2) the purging of viruses from whole blood or blood components;

(3) the treatment of psoriasis;

(4) the treatment of warts;

(5) the treatment of macular degeneration; and (6) the treatment of intra-arterial plaques.

Thus, the new phthalocyanine compositions of the present invention may be effective for a wide variety of therapeutic uses.

Dr. E. Ben-Hur and his assciates at the New York blood Center, New York N.Y., have demonstrated 11 that compounds V and VI, XIV, and XXI are effective at purging viruses from blood and/or blood components. In addition, the phthalocyanines are useful for study and research of photodynamic therapy particularly photodynamic therapy for cancer.

We claim:

1. A phthalocyanine compound having the following formula:

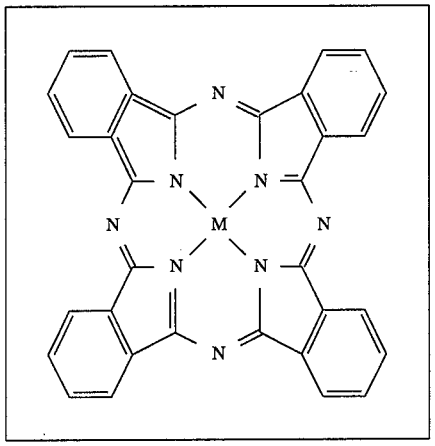

wherein M is $(G)_a Y[(OSi(CH_3)_2(CH_2)_b N_c(R')_d(R'')_e)_f X_g]_p$ wherein:

Y is selected from the group consisting of Si, Al, Ga, Ge, and Sn;

R' is selected from the group consisting of H, $CH_2$, $CH_3$, $C_2H_5$, $C_4H_9$, $C_4H_8NH$, $C_4H_8NCH_3$, $C_4H_8S$, $C_4H_8O$, $C_4H_8Se$, $CH_2CH_3$, $(CH_2)_3(CH_3)$, $OC(O)CH_3$, CS, CO, CSe, OH, $C_4H_8N(CH_2)_3CH_3$, $(CH_2)_3N(CH_3)_2$, $C(O)C_{27}H_{30}N_2O$, $(CH_2)_nN((CH_2)_o(CH_3))_2$, and an alkyl group having from 1 to 12 carbon atoms;

R'' is selected from the group consisting of H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from the group consisting of OH, $CH_3$, and $(CH_3)_3C(CH_3)_2$ SiO;

X is selected from the group consisting of: I; F; Cl; and Br;

a=0 where Y is Al or Ga, or 1 where Y is Si, Ge, or Sn;
b=an integer from 2 to 12;
c=0 or 1;
d=0, 1, 2 or 3;
e=0, 1, or 2;
f=1 or 2;
g=0 or 1;
n=an integer from 1 to 12;
o=an integer from 1 to 11; and
p=1 or 2;

where M is not $AlOSi(CH_3)_2(CH_2)_3N(CH_3)_2$;
$AlOSi(CH^3)_2(CH_2)_3N(CH_3)_3{}^+$ $I^-$;
$CH_3SiOSi(CH_3)_2(CH_2)_3N(CH_3)_2$;
$HOSiOSi(CH_3)_2(CH_2)_3N(CH_3)_2$;
$HOSiOSi(CH_3)_2(CH_2)_3N(CH_3)_3{}^+I^-$;
$Si[OSi(CH_3)_2(CH_2)_3N(CH_3)_3{}^+I^-]_2$; or
$Si[OSi(CH_3)_2(CH_2)_3N(CH_3)_2]_2$.

2. The phthalocyanine compound of claim 1, wherein M=
$Si[OSi(CH_3)_2(CH_2)_4NH_2]_2$;
$Si[OSi(CH_3)_2(CH_2)_4NHSO_2CH_3]_2$;
$HOSiOSi(CH_3)_2(CH_2)_4NHSO_2CH_3$;
$HOSiOSi(CH_3)_2(CH_2)_3N(CH_2CH_3)(CH_2)_2N(CH_3)_2$;
$Si[OSi(CH_3)_2(CH_2)_4NHCSNHC_6H_{11}O_5]_2$;
$HOSiOSi(CH_3)_2(CH_2)_3OCOCH_3$;
$Si[OSi(CH_3)_2(CH_2)_3N^+(CH_3)_2(CH_2)_{11}CH_3]_2 2I^-$;
$(CH_3)_3C(CH_3)_2SiOSiOSi(CH_3)_2(CH_2)_4NCOC_{27}H_{30}N_2O$;
$HOSiOSi(CH_3)_2(CH_2)_3OH$;
$Si[OSi(CH_3)_2(CH_2)_3N(CH_2CH_3)(CH_2)_2N(CH_3)_2]_2$;
$HOSiOSi(CH_3)_2(CH_2)_3NC_4H_8O$;
$AlOSi(CH_3)_2(CH_2)_3N^+(CH_3)_2(CH_2)_{11}CH_3I^-$;
$HOSiOSi(CH_3)_2(CH_2)_8N(CH_3)_2$;
$Si[OSi(CH_3)_2(CH_2)_3NC_4H_8O]_2$;
$HOSiOSi(CH_3)_2(CH_2)_3NC_4H_8S$;
$HOSiOSi(CH_3)_2(CH_2)_3N((CH_2)_3CH_3)_2$;
$HOSiOSi(CH_3)_2(CH_2)_3NCS$;
$HOSiOSi(CH_3)_2(CH_2)_3N[(CH_2)_3N(CH_3)_2]_2$;
$HOSiOSi(CH_3)_2(CH_2)_3NC_4H_8NCH_3$;
$Si[OSi(CH_3)_2(CH_2)_3NC_4H_8NCH_3]_2$;
$HOSiOSi(CH_3)_2(CH_2)_3NC_4H_8N(CH_2)_3CH_3$; or
$Si[OSi(CH_3)_2(CH_2)_3NC_4H_8NH]_2$.

3. The compound of claim 2 wherein M is $Si[OSi(CH_3)_2(CH_2)_4NH_2]_2$.

4. The compound of claim 2 wherein M is $Si[OSi(CH_3)_2(CH_2)_4NHSO_2CH_3]_2$.

5. The compound of claim 2 wherein M is $HOSiOSi(CH_3)_2(CH_2)_4NHSO_2CH_3$.

6. The compound of claim 2 wherein M is $HOSiOSi(CH_3)_2(CH_2)_3N(CH_2CH_3)(CH_2)_2N(CH_3)_2$.

7. The compound of claim 2 wherein M is $Si[OSi(CH_3)_2(CH_2)_4NHCSNHC_6H_{11}O_5]_2$.

8. A phthalocyanine compound having the following formula $SiPc[OSi(CH_3)_2(CH_2)_3N(CH_3)_2]_2$.

9. The compound of claim 2 wherein M is $HOSiOSi(CH_3)_2(CH_2)_3OCOCH_3$.

10. The compound of claim 2 wherein M is $Si[OSi(CH_3)_2(CH_2)_3N^+(CH_3)_2(CH_2)_{11}CH_3]_2 2I^-$.

11. The compound of claim 2 wherein M is $(CH_3)_3C(CH_3)_2SiOSiOSi(CH_3)_2(CH_2)_4NCOC_{27}H_{30}N_2O$.

12. The compound of claim 2 wherein M is $HOSiOSi(CH_3)_2(CH_2)_3OH$.

13. The compound of claim 2 wherein M is $Si[OSi(CH_3)_2(CH_2)_3N(C_2H_5)(CH_2)_2N(CH_3)_2]_2$.

14. The compound of claim 2 wherein M is $HOSiOSi(CH_3)_2(CH_2)_3NC_4H_8O$.

15. The compound of claim 2 wherein M $AlOSi(CH_3)_2(CH_2)_3N^+(CH_3)_2(CH_2)_{11}CH_3I^-$.

16. The compound of claim 2 wherein M is $HOSiOSi(CH_3)_2(CH_2)_8N(CH_3)_2$.

17. The compound of claim 2 wherein M is $Si[OSi(CH_3)_2(CH_2)_3NC_4H_8O]_2$.

18. The compound of claim 2 wherein M is $HOSiOSi(CH_3)_2(CH_2)_3NC_4H_8S$.

19. The compound of claim 2 wherein M is $HOSiOSi(CH_3)_2(CH_2)_3N((CH_2)_3CH_3)_2$.

20. The compound of claim 2 wherein M is $HOSiOSi(CH_3)_2(CH_2)_3NCS$.

21. The compound of claim 2 wherein M is $HOSiOSi(CH_3)_2(CH_2)_3N[(CH_2)_3N(CH_3)_2]_2$.

22. The compound of claim 2 wherein M is $HOSiOSi(CH_3)_2(CH_2)_3NC_4H_8NCH_3$.

23. The compound of claim 2 wherein M is $Si[OSi(CH_3)_2(CH_2)_3NC_4H_8NCH_3]_2$.

24. The compound of claim 2 wherein M is $HOSiOSi(CH_3)_2(CH_2)_3NC_4H_8N(CH_2)_3CH_3$.

25. The compound of claim 2 wherein M is Si[OSi(CH$_3$)$_2$(CH$_2$)$_3$NC$_4$H$_8$NH]$_2$.

26. A therapeutic composition comprising the phthalocyanine of claim 1 and a pharmaceutical carrier therefor.

27. A method for treating fibrosarcomas squamous cell carcinoma, and skin tumors comprising the steps of administering, to a patient an effective amount of the phthalocyanine of claim 1, and applying light of sufficient wave length and intensity to the fibrosarcoma, squamous cell carcinoma or skin tumor to activate said phthalocyanine, wherein said activated phthalocyanine exerts a cyotoxic effect on said fibrosarcoma, squamous cell carcinoma or skin tumor.

28. The method of claim 27, wherein said light is of the visible spectrum above about 600 nm.

29. The method of claim 27, wherein the M group of said phthalocyanine is HOSiOSi(CH$_3$)$_2$(CH$_2$)$_4$NHSO$_3$CH$_3$.

30. A method for treating fibrosarcomas, squamous cell carcinoma and skin tumors comprising the steps of administering an effective amount of a phthalocyanine wherein the phthalocyanine is HOSiPcOSi(CH$_3$)$_2$(CH$_2$)$_3$N(CH$_3$)$_2$, and applying light of sufficient wave length and intensity to the fibrosarcoma, squamous cell carcinoma or skin tumor to activate said phthalocyanine, wherein said activated phthalocyanine exerts a cytotoxic effect on said fibrosarcoma, squamous cell carcinoma or skin tumor.

31. A method for treating fibrosarcomas, squamous cell carcinoma, and skin tumors comprising the steps of administering, to a patient, an effective amount of a phthalocyanine, and applying light of sufficient wave length and intensity tot he fibrosarcoma, squamous cell carcinoma or skin tumor to activate said phthalocyanine, wherein said activated phthalocyanine exerts a cytotoxic effect on said fibrosarcoma, squamous cell carcinoma or skin tumor and wherein said phathalocyanine is SiPc [OSi(CH$_3$)$_2$(CH$_2$)$_3$N(CH$_3$)$_2$]$_2$.

32. The method of claim 27, wherein the M group of said phthalocyanine is Si[OSi(CH$_3$)$_2$(CH$_2$)$_3$N(C$_2$H$_5$)(CH$_2$)$_2$N(CH$_3$)$_2$]$_2$.

33. The method of claim 27, wherein said phthalocyanine is HOSiPcOSi(CH$_3$)$_2$(CH$_2$)$_3$NC$_4$H$_8$NCH$_3$.

34. A phthalocyanine compound having the following formula: CH$_3$SiPcOSi(CH$_3$)$_2$(CH$_2$)$_3$N(CH$_3$)$_2$.

35. A phthalocyanine compound having the following formula:

SiPc[OSi(CH$_3$)$_2$(CH$_2$)$_3$N(CH$_3$)$_3^+$I$^-$]$_2$.

* * * * *

(12) REEXAMINATION CERTIFICATE (4341st)
United States Patent
Kenney et al.

(10) Number: US 5,484,778 C1
(45) Certificate Issued: *May 8, 2001

(54) PHTHALOCYANINE PHOTOSENSITIZERS FOR PHOTODYNAMIC THERAPY AND METHODS FOR THEIR USE

(75) Inventors: Malcolm E. Kenney, Cleveland Heights; Nancy L. Oleinick, University Heights, both of OH (US); Boris D. Rihter, Wauwatosa, WI (US); Ying-Syi Li, Cleveland Heights, OH (US)

(73) Assignee: University Hospitals of Cleveland, Cleveland, OH (US)

Reexamination Request:
No. 90/004,733, Aug. 27, 1997

Reexamination Certificate for:
Patent No.: 5,484,778
Issued: Jan. 16, 1996
Appl. No.: 08/116,259
Filed: Sep. 2, 1993

(*) Notice: This patent is subject to a terminal disclaimer.

Related U.S. Application Data

(63) Continuation-in-part of application No. 07/980,494, filed on Nov. 23, 1992, now abandoned, which is a continuation of application No. 07/554,290, filed on Jul. 17, 1990, now Pat. No. 5,166,197.

(51) Int. Cl.[7] .......................... C09B 47/04; C09B 47/08; A61K 31/555; A61K 31/685
(52) U.S. Cl. .............. 514/63; 514/43; 514/185; 514/191; 536/29.11; 540/123; 540/125; 540/128; 540/140
(58) Field of Search ................. 514/43, 63, 185, 514/191; 540/123, 125, 128, 140; 536/29.11

(56) References Cited

PUBLICATIONS

"Photodynamic effects of silicon phthalocyanines in models cells and tumors" by Olenick et al., SPIE vol. 1645 Optical Methods for Tumor Treatment and Detection (1992); pp 242–250, Jan. 20, 1992.

Oleinick, in "Optical Methods for Tumor Treatment and Detection; Mechanisms and Techniques in Photodynamic Therapy", vol. 1645, pp 242–250 (SPIE, Bellingham, WA), 1992.*

Megerian, Laryngoscope, vol. 103, pp 967–975, Sep. 1993.*

* cited by examiner

*Primary Examiner*—Mark L Berch

(57) ABSTRACT

The present invention relates to a series of novel phthalocyanine compositions (or compounds) suitable for use as photosensitizers for photodynamic therapy. Specifically, the invention relates to a series of new aluminum (Al) germanium (Ge), gallium (Ga), tin (Sn) and/or silicon (Si) phthalocyanines having substituted amine or quaternary ammonium axial ligands attached to the central metal, and the use of these new phthalocyanine compositions for the treatment of cancer through photosensitization. Moreover, the present invention is directed to the methods of preparing these compositions for use in photodynamic therapy.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 31 and 34–35 is confirmed.

Claims 1 and 30 are determined to be patentable as amended.

Claims 2–29 and 32–33, dependent on an amended claim, are determined to be patentable.

New claims 36 and 37 are added and determined to be patentable.

1. A phthalocyanine compound having the following formula:

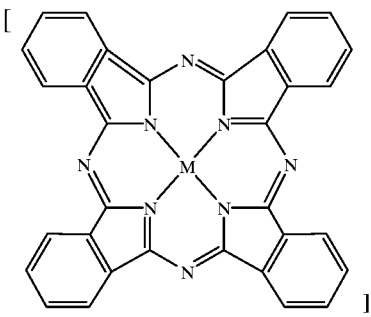

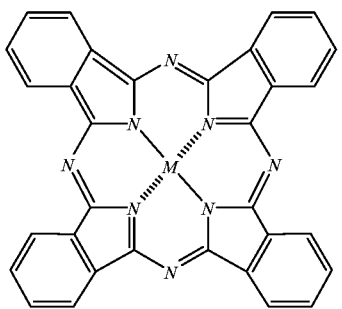

wherein

M is $(G)_a Y[(OSi(CH_3)_2(CH_2)_b N_c(R')_d(R'')_e)_f X_g]_p$ wherein:

Y is selected from the group consisting of Si, Al, Ga, Ge, and Sn;

R' is selected from the group consisting of H, $CH_2$, $CH_3$, $C_2H_5$, $C_4H_9$, $C_4H_8NH$, $C_4H_8NCH_3$, $C_4H_8S$, $C_4H_8O$, $C_4H_8Se$, $CH_2CH_3$, $(CH_2)_3(CH_3)$, $OC(O)CH_3$, CS, CO, CSe, OH, $C_4H_8N(CH_2)_3CH_3$, $(CH_2)_3N(CH_3)_2$, $C(O)C_{27}H_{30}N_2O$, $(CH_2)_nN((CH_2)_o(CH_3))_2$, and an alkyl group having from 1 to 12 carbon atoms;

R" is selected from the group consisting of H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from the group consisting of OH, $CH_3$, and $(CH_3)_3C(CH_3)_2SiO$;

X is selected from the group consisting of: I; F; Cl; and Br;

a=0 where Y is Al or Ga[,]*;*

*a=0 where Y is Si, Ge, or Sn and p=2;*

*or a=1 where Y is Si, Ge, or Sn and p=1;* b=an integer from 2 to 12;

c=0 or 1;

d=0, 1, 2 or 3;

e=0, 1, or 2;

f=1 or 2;

g=0 or 1;

n=an integer from 1 to 12;

o=an integer from 1 to 11; and p=1 or 2;

where

M is not $[AlOSi(CH_3)_2(CH_2)_3N(CH_3)_2$; $AlOSi(CH^3)_2(CH_2)_3N(CH_3)_3{}^+I^-$; $CH_3SiOSi(CH_3)_2(CH_2)_3N(CH_3)_2$; $HOSiOSi(CH_3)_2(CH_2)_3N(CH_3)_2$; $HOSiOSi(CH_3)_2(CH_2)_3N(CH_3)_3{}^+I^-$; $Si[OSi(CH_3)_2(CH_2)_3N(CH_3)_3{}+I^-]_2$; or $Si[OSi(CH_3)_2(CH_2)_3N(CH_3)_2]_2]$ *$AlOSi(R1)_2(CH_2)_wN(R2)_2$; $AlOSi(R1)_2(CH_2)_wN(R2)_3{}^+R3^-$; $CH_3SiOSi(R1)_2(CH_2)_wN(R2)_2$; $CH_3SiOSi(R1)_2(CH_2)_wN(R2)_3{}^+R3^-$; $HOSiOSi(R1)_2(CH_2)_wN(R2)_2$; $HOSiOSi(R1)_2(CH_2)_wN(R2)_3{}^+R3^-$; $Si[OSi(R1)_2(CH_2)_wN(R2)_2]_2$, or $Si[OSi(R1)_2(CH_2)_wN(R2)_3{}^+R3]_2$;*

*wherein*

*R1 is a methyl or ethyl group*

*R2 is a methyl or ethyl group*

*R3 is I, Cl, or Br; and*

*w=an integer from 2 to 4.*

30. A method for treating [fibrosarcomas,] squamous cell carcinoma [and skin tumors] comprising the steps of administering an effective amount of a phthalocyanine wherein the phthalocyanine is $HOSiPcOSi(CH_3)_2(CH_2)_3N(CH_3)_2$, and applying light of sufficient wave length and intensity to the [fibrosarcoma,] squamous cell carcinoma [or skin tumor] to activate said phthalocyanine, wherein said activated phthalocyanine exerts a cytotoxic effect on said [fibrosarcoma,] squamous cell carcinoma [or skin tumor].

*36. A method for treating skin tumors comprising the steps of*

*(a) administering an effective amount of a phthalocyanine compound having the following formula:*

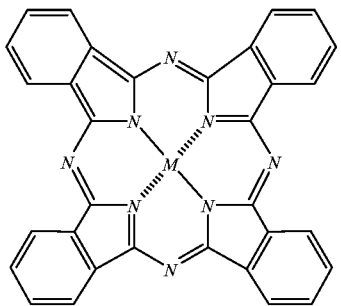

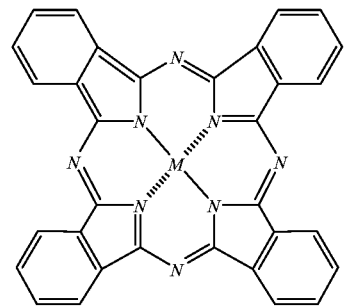

wherein

M is $(G)_a Y[(OSi(CH_3)_2(CH_2)_b N_c(R')_d(R'')_e)_f X_g]_p$, wherein:

Y is selected from the group consisting of Si, Al, Ga, Ge, and Sn;

R' is selected from the group consisting of H, $CH_2$, $CH_3$, $C_2H_5$, $C_4H_9$, $C_4H_8NH$, $C_4H_8NCH_3$, $C_4H_8S$, $C_4H_8O$, $C_4H_8Se$, $CH_2CH_3$, $(CH_2)_3(CH_3)$, $OC(O)CH_3$, $CS$, $CO$, $CSe$, $OH$, $C_4H_8N(CH_2)_3CH_3$, $(CH_2)_3N(CH_3)_2$, $C(O)C_{27}H_{30}N_2O$, $(CH_2)_n N((CH_2)_o(CH_3))_2$, and an alkyl group having from 1 to 12 carbon atoms;

R'' is selected from the group consisting of H, $SO_2CH_3$, $(CH_2)_2N(CH_3)_2$, $(CH_2)_{11}CH_3$, $C(S)NHC_6H_{11}O_5$, $(CH_2)_n N((CH_2)_o(CH_3))_2$, and an alkyl group having from 1 to 12 carbon atoms;

G is selected from the group consisting of OH, $CH_3$, and $(CH_3)_3C(CH_3)_2SiO$;

X is selected from the group consisting of: I; F; Cl; and Br;

$a=0$ where Y is Al or Ga;

$a=0$ where Y is Si, Ge, or Sn and $p=2$;

$a=1$ where Y is Si, Ge, or Sn and $p=1$;

$b=$ an integer from 2 to 12;

$c=0$ or 1;

$d=0$, 1, 2 or 3;

$e=0$, 1, or 2;

$f=1$ or 2;

$g=0$ or 1;

$n=$ an integer from 1 to 12;

$o=$ an integer from 1 to 11; and $p=1$ or 2;

where

M is not $AlOSi(CH_3)_2(CH_2)_3N(CH_3)_2$, $AlOSi(CH_3)_2(CH_2)_3N(CH_3)_3^+I^-$, $CH_3SiOSi(CH_3)_2(CH_2)_3N(CH_3)_2$, $HOSiOSi(CH_3)_2(CH_2)_3N(CH_3)_2$, $HOSiOSi(CH_3)_2(CH_2)_3N(CH_3)_3^+I^-$, $Si[OSi(CH_3)_2(CH_2)_3N(CH_3)_3^+I^-]_2$, or $Si[OSi(CH_3)_2(CH_2)_3N(CH_3)_2]_2$; and (b) applying light of sufficient wave length and intensity to the skin tumor to activate said phthalocyanine, wherein said activated phthalocyanine exerts a cytotoxic effect on said skin tumor.

37. A method for treating squamous cell carcinoma comprising the steps of (a) administering an effective amount of a phthalocyanine compound having the following formula:

wherein

M is $(G)_a Y[(OSi(CH_3)_2(CH_2)_b N_c(R')_d(R'')_e)_f X_g]_p$, wherein:

Y is selected from the group consisting of Si, Al, Ga, Ge, and Sn;

R' is selected from the group consisting of H, $CH_2$, $CH_3$, $C_2H_5$, $C_4H_9$, $C_4H_8NH$, $C_4H_8NCH_3$, $C_4H_8S$, $C_4H_8O$, $C_4H_8Se$, $CH_2CH_3$, $(CH_2)_3(CH_3)$, $OC(O)CH_3$, $CS$, $CO$, $CSe$, $OH$, $C_4H_8N(CH_2)_3CH_3$, $(CH_2)_3N(CH_3)_2$, $C(O)C_{27}H_{30}N_2O$, $(CH_2)_n N((CH_2)_o(CH_3))_2$, and an alkyl group having from 1 to 12 carbon atoms;

R'' is selected from the group consisting of H, $SO_2CH_3$, $(CH_2)_2N(CH_3)_2$, $(CH_2)_{11}CH_3$, $C(S)NHC_6H_{11}O_5$, $(CH_2)_n N((CH_2)_o(CH_3))_2$, and an alkyl group having from 1 to 12 carbon atoms;

G is selected from the group consisting of OH, $CH_3$, and $(CH_3)_3C(CH_3)_2SiO$;

X is selected from the group consisting of: I; F; Cl; and Br;

$a=0$ where Y is Al or Ga, $a=0$ where Y is Si, Ge, or Sn and $p=2$;

$a=1$ where Y is Si, Ge, or Sn and $p=1$;

$b=$ an integer from 2 to 12;

$c=0$ or 1;

$d=0$, 1, 2 or 3;

$e=0$, 1, or 2;

$f=1$ or 2;

$g=0$ or 1;

$n=$ an integer from 1 to 12;

$o=$ an integer from 1 to 11; and $p=1$ or 2;

where

M is not $AlOSi(CH_3)_2(CH_2)_3N(CH_3)_2$, $AlOSi(CH_3)_2(CH_2)_3N(CH_3)_3^+I^-$, $CH_3SiOSi(CH_3)_2(CH_2)_3N(CH_3)_2$, $HOSiOSi(CH_3)_2(CH_2)_3N(CH_3)_2$, $HOSiOSi(CH_3)_2(CH_2)_3N(CH_3)_3^+I^-$, $Si[OSi(CH_3)_2(CH_2)_3N(CH_3)_3^+I^-]_2$, or $Si[OSi(CH_3)_2(CH_2)_3N(CH_3)_2]_2$; and (b) applying light of sufficient wave length and intensity to the squamous cell carcinoma to activate said phthalocyanine, wherein said activated phthalocyanine exerts a cytotoxic effect on said squamous cell carcinoma.

\* \* \* \* \*